(12) United States Patent
Tatarkiewicz et al.

(10) Patent No.: US 10,161,852 B2
(45) Date of Patent: Dec. 25, 2018

(54) SPECIAL PURPOSE CUVETTE ASSEMBLY AND METHOD FOR OPTICAL MICROSCOPY OF NANOPARTICLES IN LIQUIDS

(71) Applicant: MANTA Instruments, Inc., San Diego, CA (US)

(72) Inventors: Jan J. Tatarkiewicz, San Diego, CA (US); Rick Cooper, San Diego, CA (US)

(73) Assignee: MANTA INSTRUMENTS, INC., San Diego, CA (US)

( * ) Notice: Subject to any disclaimer, the term of this patent is extended or adjusted under 35 U.S.C. 154(b) by 0 days.

(21) Appl. No.: 15/594,967

(22) Filed: May 15, 2017

(65) Prior Publication Data
US 2017/0343469 A1 Nov. 30, 2017

Related U.S. Application Data

(63) Continuation-in-part of application No. 15/399,679, filed on Jan. 5, 2017, now abandoned, and a continuation-in-part of application No. 15/293,180, filed on Oct. 13, 2016, now Pat. No. 10,012,580, and a continuation-in-part of application No. 15/018,532, filed on Feb. 8, 2016, now Pat. No. 9,909,972.

(60) Provisional application No. 62/421,585, filed on Nov. 14, 2016, provisional application No. 62/372,025, filed on Aug. 8, 2016, provisional application No. 62/357,777, filed on Jul. 1, 2016.

(51) Int. Cl.
*G01N 21/03* (2006.01)
*G01N 15/02* (2006.01)
*G01N 15/00* (2006.01)

(52) U.S. Cl.
CPC ..... *G01N 21/0303* (2013.01); *G01N 15/0211* (2013.01); *G01N 2015/0038* (2013.01); *G01N 2015/0053* (2013.01); *G01N 2021/0307* (2013.01)

(58) Field of Classification Search
CPC . G01N 21/0303; G01N 15/0211; G01N 21/00
USPC .................................................. 356/342
See application file for complete search history.

(56) References Cited

U.S. PATENT DOCUMENTS

| 5,093,866 A * | 3/1992 | Douglas-Hamilton ..................... G01N 15/1456 356/39 |
| 6,737,021 B2 * | 5/2004 | Watari ................ B01F 11/0283 366/127 |

(Continued)

*Primary Examiner* — Roy M Punnoose
(74) *Attorney, Agent, or Firm* — Manuel de la Cerra

(57) ABSTRACT

A system for emitting and detecting electromagnetic radiation of multiple wavelengths to observe the motion of particles in a polydisperse solution in order to size the particles is provided. The system includes a first and second light sources constructed to emit a first and second beams of electromagnetic radiation at substantially a first and second wavelength, respectively. The beams are directed to a specimen chamber such that a portion of the beams scatter when illuminating the particles, and wherein the scattered portion of the beams are directed to a sensor. The first and second wavelengths are different from each other and a recorder is connected to the sensor. At processor controls the light sources in a time-division fashion, and from the resulting images the size of particles can be determined by tracking the motion of the particles.

20 Claims, 20 Drawing Sheets

(56) References Cited

U.S. PATENT DOCUMENTS

| | | | |
|---|---|---|---|
| 8,842,274 B2* | 9/2014 | Harnack | B01L 3/5088 |
| | | | 356/246 |
| 9,025,144 B2* | 5/2015 | Knox | G01N 15/06 |
| | | | 356/338 |
| 9,279,761 B1* | 3/2016 | Sternick | G01N 21/03 |
| 9,291,634 B2* | 3/2016 | Katou | B01F 11/0283 |
| 2010/0262374 A1* | 10/2010 | Hwang | B82Y 30/00 |
| | | | 702/19 |
| 2014/0193892 A1* | 7/2014 | Mohan | G01N 21/05 |
| | | | 435/287.2 |
| 2014/0273188 A1* | 9/2014 | Mohan | G01N 21/0303 |
| | | | 435/287.2 |

* cited by examiner

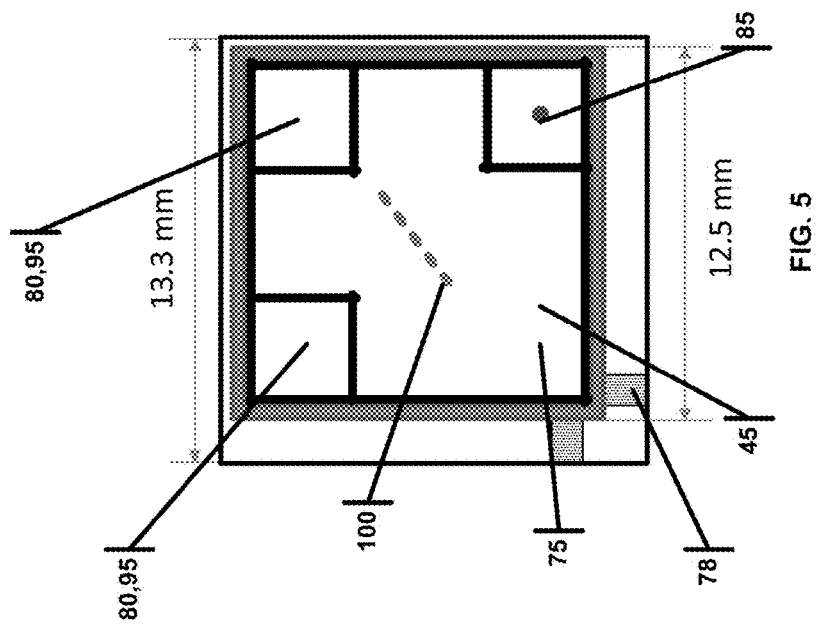
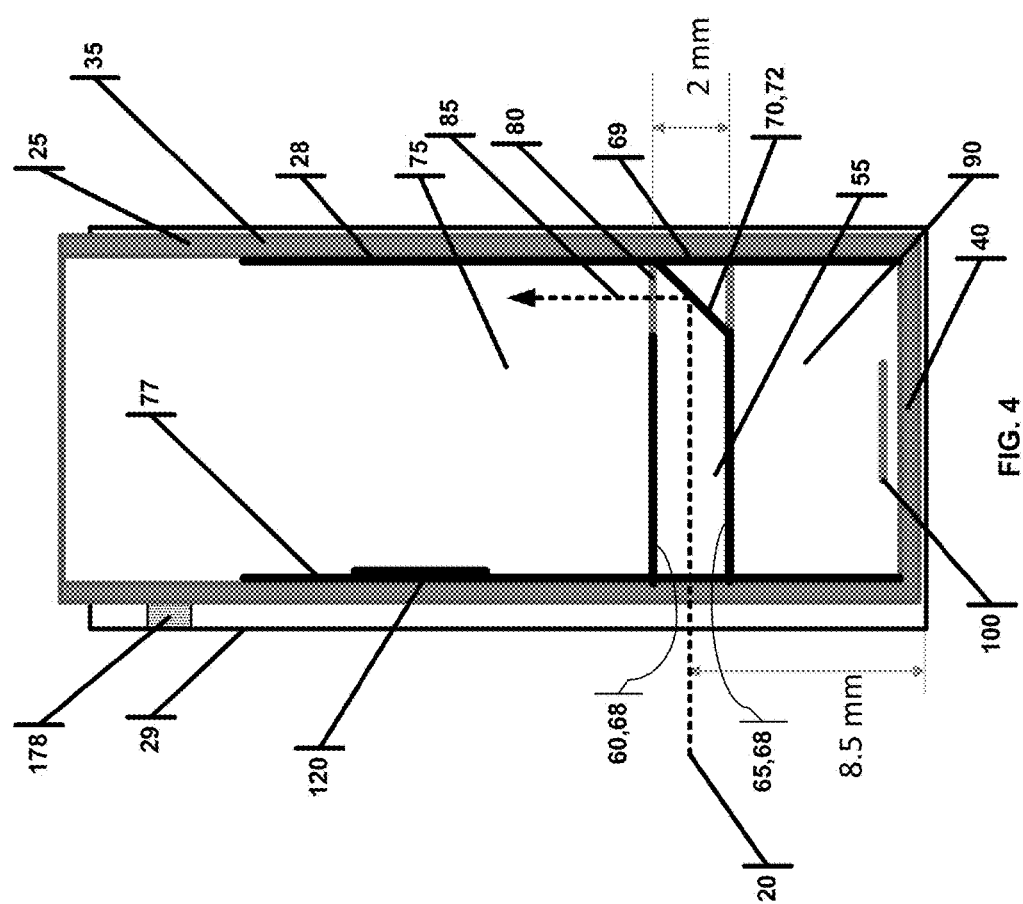

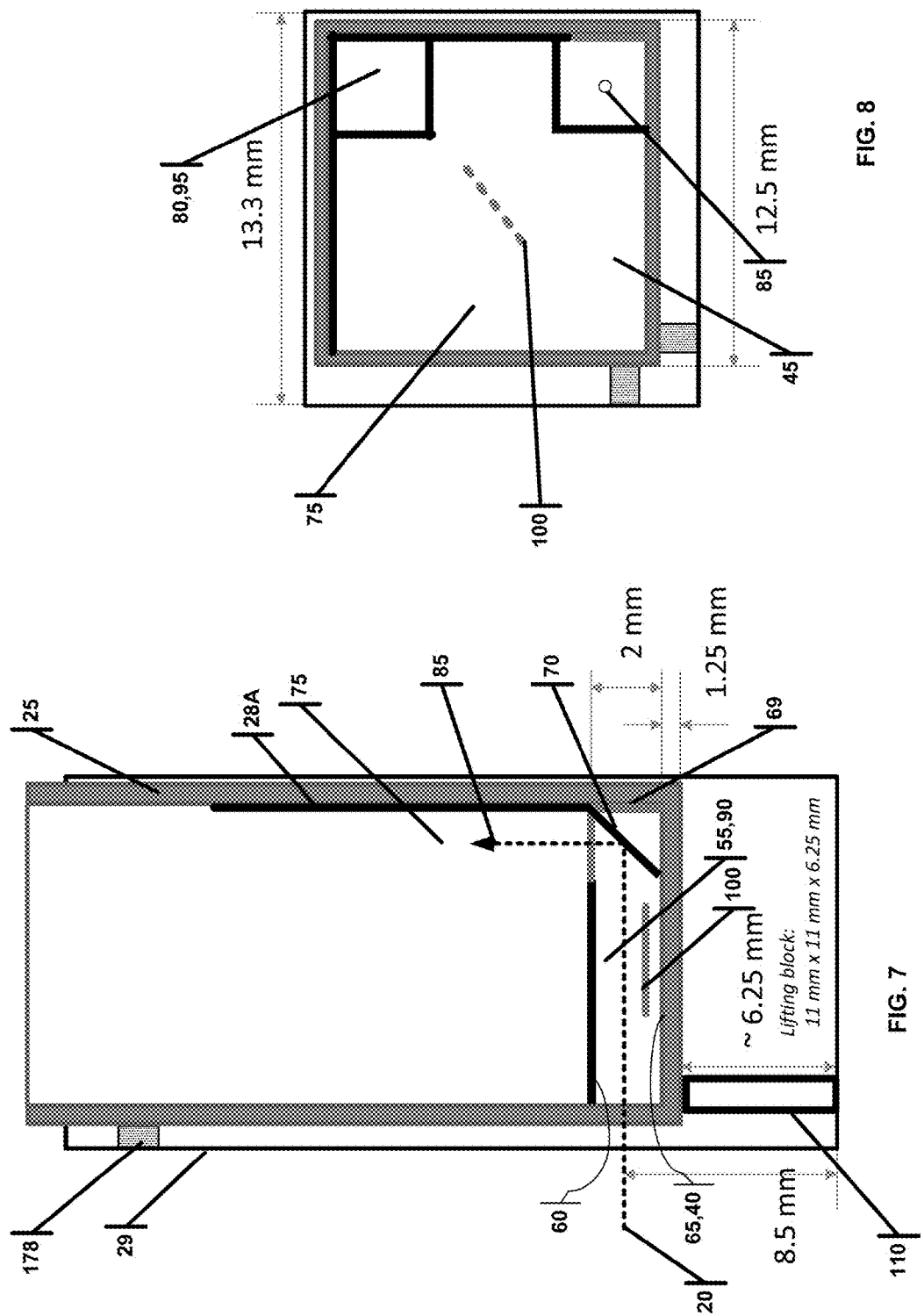

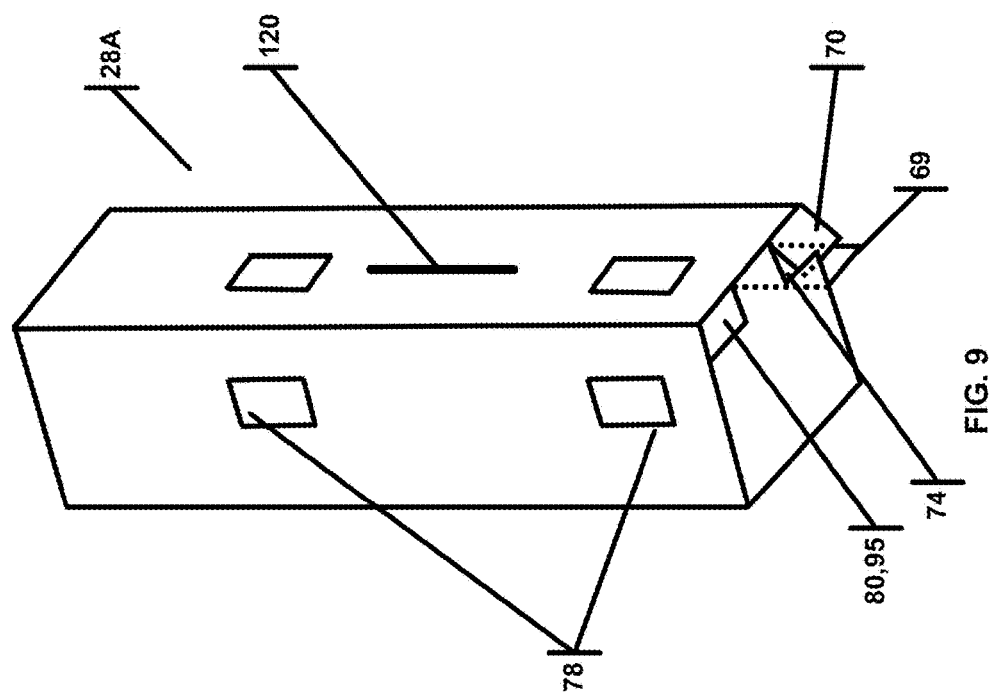

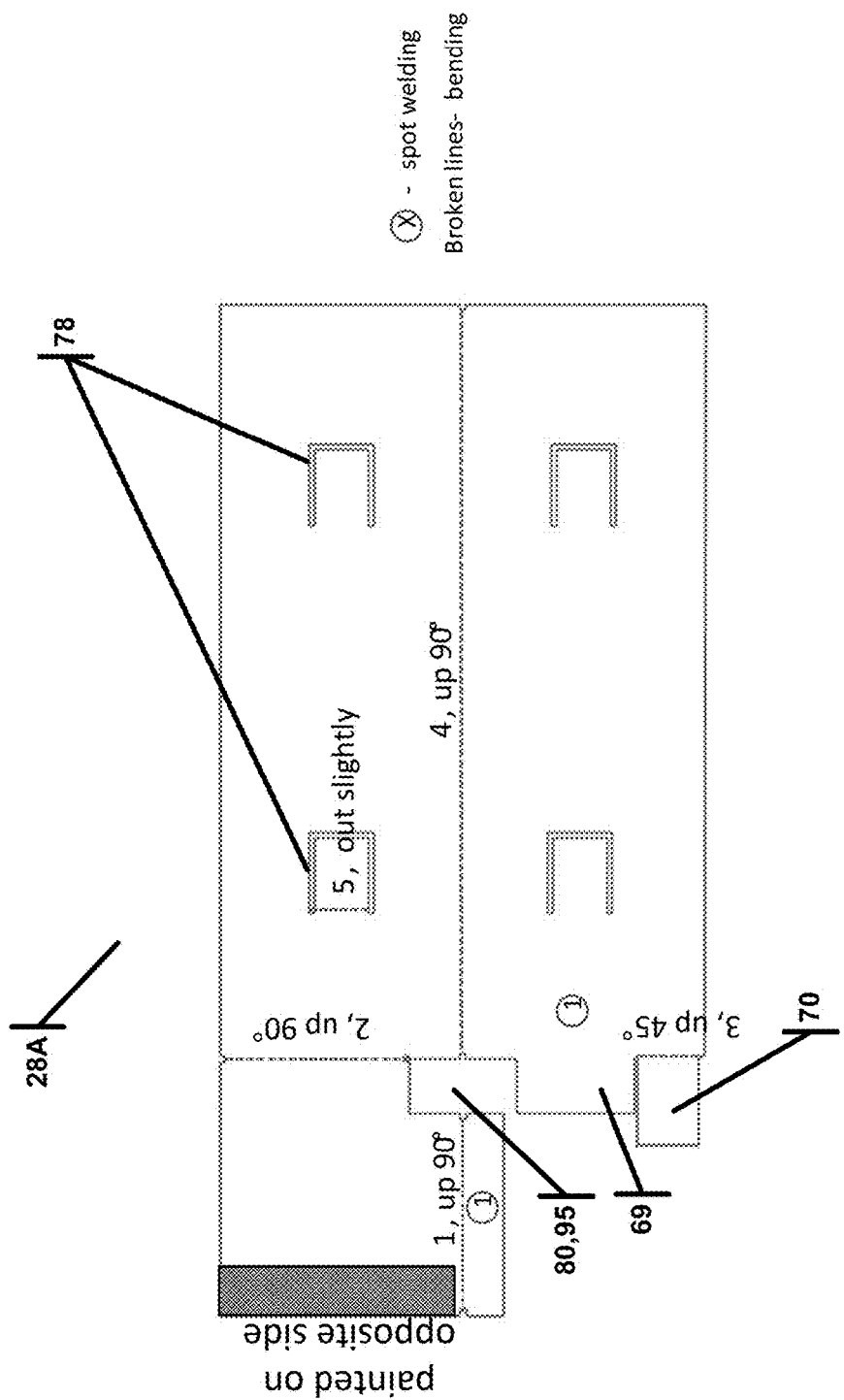

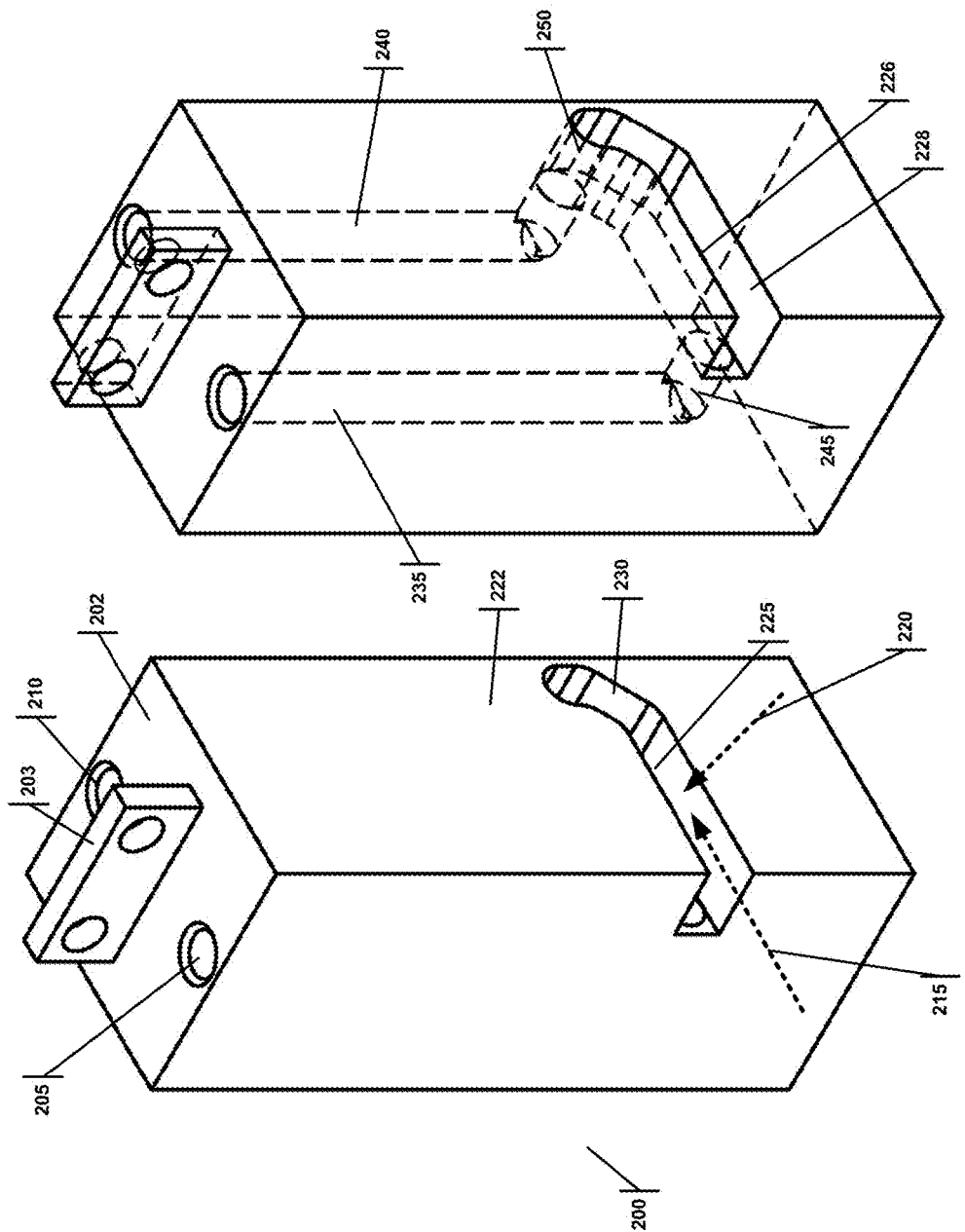

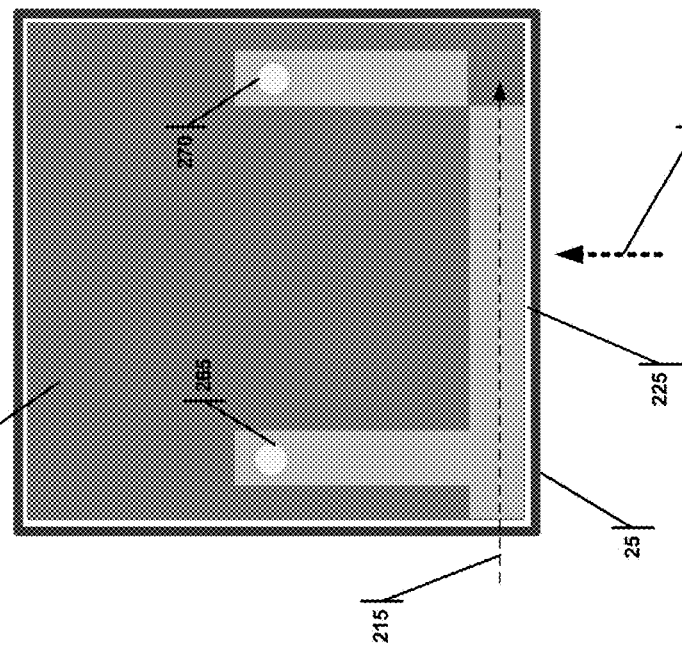
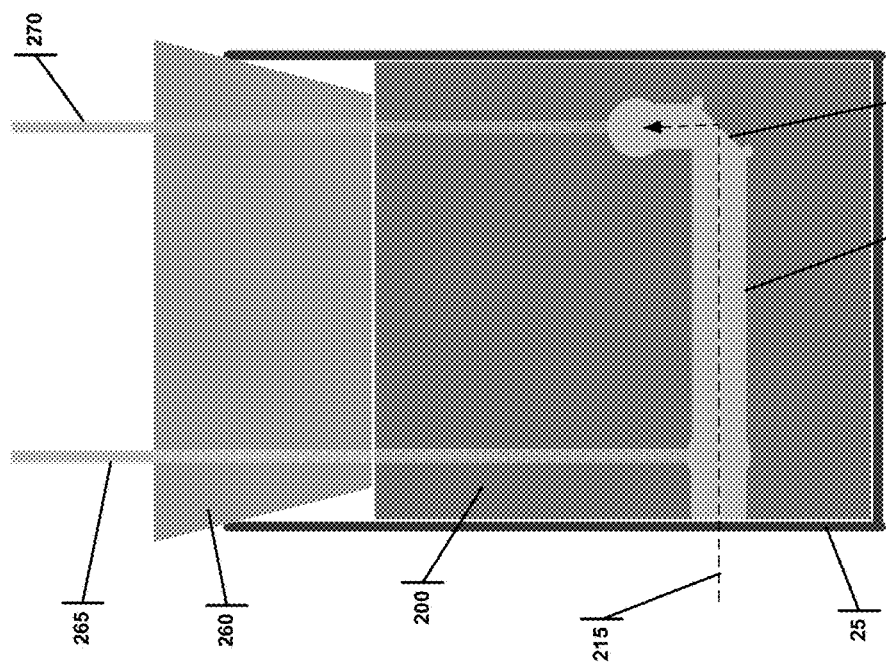
FIG. 17A Side View
FIG. 17B Top View

SPECIAL PURPOSE CUVETTE ASSEMBLY AND METHOD FOR OPTICAL MICROSCOPY OF NANOPARTICLES IN LIQUIDS

1.0 RELATED APPLICATIONS

This application claims priority as a continuation-in-part of U.S. patent application Ser. No. 15/399,679, filed on Jan. 5, 2017, titled "SPECIAL PURPOSE CUVETTE ASSEMBLY AND METHOD FOR OPTICAL MICROSCOPY OF NANOPARTICLES IN LIQUIDS" which claimed priority as a continuation of U.S. patent application Ser. No. 15/194,823, filed on Jun. 28, 2016, titled "SPECIAL PURPOSE CUVETTE ASSEMBLY AND METHOD FOR OPTICAL MICROSCOPY OF NANOPARTICLES IN LIQUIDS" issued on Jan. 10, 2017 as U.S. Pat. No. 9,541,490, which claimed priority as the non-provisional of U.S. Provisional Patent Application No. 62/187,391, filed on Jul. 1, 2015, titled "SPECIAL PURPOSE CUVETTE ASSEMBLY AND METHOD FOR OPTICAL MICROSCOPY OF NANOPARTICLES IN LIQUIDS," this application also claims priority as a continuation-in-part of U.S. patent application Ser. No. 15/018,532 filed on Feb. 8, 2016, titled "MULTI-CAMERA APPARATUS FOR OBSERVATION OF MICROSCOPIC MOVEMENTS AND COUNTING OF PARTICLES IN COLLOIDS AND ITS CALIBRATION", this application also claims priority as a continuation-in-part of U.S. patent application Ser. No. 15/293,180 filed on Oct. 13, 2016, titled "APPARATUS AND METHOD FOR MEASUREMENT OF GROWTH OR DISSOLUTION KINETICS OF COLLOIDAL PARTICLES", this application also claims priority as a non-provisional of U.S. Patent Application No. 62/357,777 filed on Jul. 1, 2016, titled "METHOD FOR CALIBRATING INVESTIGATED VOLUME FOR LIGHT SHEET BASED NANOPARTICLE TRACKING AND COUNTING APPARATUS"; as non-provisional of U.S. Patent Application No. 62/372,025, filed on Aug. 8, 2016, titled "METHOD FOR CALIBRATING INVESTIGATED VOLUME FOR LIGHT SHEET BASED NANOPARTICLE TRACKING AND COUNTING APPARATUS"; and as non-provisional of U.S. Provisional Patent Application No. 62/421,585, filed on Nov. 14, 2016, titled "METHOD FOR CALIBRATING INVESTIGATED VOLUME FOR LIGHT SHEET BASED NANOPARTICLE TRACKING AND COUNTING APPARATUS" the disclosures of which are herein incorporated by reference in their entirety.

This application is also related to U.S. patent application Ser. No. 14/730,138, filed on Jun. 3, 2015, titled "NANOPARTICLE ANALYZER," U.S. patent application Ser. No. 15/018,532 filed on Feb. 8, 2016, the disclosure of which is herein incorporated by reference in its entirety.

2.0 TECHNICAL FIELD

The present invention relates to a system for detecting and measuring nanoparticles in liquid samples.

3.0 BACKGROUND

Nanoparticles are ubiquitous and by far the most abundant particle-like entities found in natural environments and are widespread across many applications associated with human activities. There are many types of naturally occurring nanoparticles and man-made (engineered) nanoparticles. Nanoparticles occur in air, aquatic environments, rain water, drinking water, bio-fluids, pharmaceuticals, drug delivery and therapeutic products, and a broad range of many industrial products. Nanoparticles usually occur within polydisperse assemblages which are characterized by co-occurrence of differently-sized particles.

Given the widespread use of nanoparticles, the ability to control and accurately characterize their properties may be useful to many applications. Conventional methods for measuring nanoparticle properties include Nanoparticle Tracking Analysis, which uses a microscope and video camera to analyze frames of the recorded videos to track images of light reflected or scattered by the nanoparticles undergoing Brownian motion. The instrument to perform such analysis is usually comprised of a small cell, or cuvette, that enables illumination of a liquid with a very precisely defined, narrow light sheet and observation of scattered light from the nanoparticles, usually at a 90-degree angle to the light sheet. Hence the cuvette must contain at least two surfaces with minimal light attenuation properties (for example optical glass). Such cuvettes are widely used in all types of optical measurements in various laboratory instruments, are easily available and have standardized internal dimensions (in the case of the prototype 10 mm×10 mm×45 mm).

Ideally there should be no bulk movement of the liquid when the videos are being recorded so the only observed particle motion is Brownian motion. However, due to the low thermal conductivity of glass and because of potentially considerable energy transmitted from the illuminating beam to the liquid and wall of cuvette by absorption, one can observe thermally generated micro flow of the liquid regardless of the volume of liquid in a traditional cuvette. Other sources of micro flows are possible, for example movements of the table on which the instrument is mounted that cause vibrations of the table or evaporation of the sample liquid that cools its surface. Flow can also be induced by stirring the liquid in the cuvette, or by pumping liquids in and out of the cuvette. In these and other induced flow cases, it is desirable to arrest the flow as quickly as possible for effective and timely particle analysis. Algorithms are available to detect and remove effects of such bulk liquid movement; however, these algorithms have limitations and more accurate results are achieved in the absence of bulk liquid movement.

Another desirable situation for optimal detection and processing of scattered light from nanoparticles in liquids is to minimize or eliminate backscattering of light from the wall of the cuvette that is opposite to the wall where light enters the cuvette (the back wall). Such backscattering of the incoming light beam typically broadens the illuminated region (thickening of light sheet), thus creating images that could be partially out of focus of the microscope (fuzzy images), which are not suitable for precise particle tracking. Backscattering induced broadening has an inherently inconsistent impact on the width of the light sheet and as such also causes variability in particle concentration measurements since the width of the light sheet effects the volume of sample that is being analyzed in each measurement. Secondarily deleterious light scattering effects from other reflective surfaces in the cuvette should also be minimized through use of light absorbing materials or coatings (such as black paint).

Another important consideration is compatibility with existing components that accurately hold the cuvette in place relative to the light sheet, control its temperature and enable stirring and or pumping of the liquid. Such stirring and/or pumping facilitates examination of multiple fresh aliquots from the same sample within the cuvette and is easily achieved with a magnetic stirring bar at the bottom of the cuvette which is driven by an external rotating magnet, or with an external pump.

What is needed, therefore, is an improved system that can minimize movement of the liquid while also eliminating backscatter of the light within the observation region of the cuvette.

4.0 SUMMARY

The apparatus, systems, and methods described herein elegantly solve the movement and backscatter problems and provide other improvements and benefits as will be apparent to persons of skill in the art. Accordingly, a system for emitting and detecting electromagnetic radiation of multiple wavelengths to observe the motion of particles in a polydisperse solution in order to size the particles is provided. The system includes a first and second light sources constructed to emit a first and second beams of electromagnetic radiation at substantially a first and second wavelength, respectively. The beams are directed to a specimen chamber such that a portion of the beams scatter when illuminating the particles, and wherein the scattered portion of the beams are directed to a sensor. The first and second wavelengths are different from each other and a recorder is connected to the sensor. A processor connected to the light sources and the recorder. The processor performs the following steps: (a)(1) illuminating the specimen chamber with the first beam; (a)(2) preventing the second beam from illuminating the chamber; and (a)(3) simultaneously recording an image including the scattered portion of the first beam from the sensor to an image file; after step (a): (b)(1) illuminating the specimen chamber with the second beam; (b)(2) preventing the first beam from illuminating the chamber; and (b)(3) simultaneously recording an image including the scattered portion of the second beam from the sensor to the image file; repeating steps (a) and (b) until the expiration of a time period; extracting the images from step (a) into a first extracted image file; extracting the images from step (b) into a second extracted image file; determining the size of particles within the first extracted image file by tracking the motion of particles within the first extracted image file; and determining the size of particles within the second extracted image file by tracking the motion of particles within the second extracted image file.

The system may include a combining structure, such as a dichroic mirror, that merges the first and second beams into the same optical path before either light beam reaches the specimen chamber. The system may also have a light sheet former that forms the first and second beams into a sheet of electromagnetic radiation directed at the specimen chamber. The system may have an imaging objective that focuses the scattered portion of the first and second beams onto the sensor.

The recorder may have a frame rate and the exposure time is correlated to the frame rate. The sensor may be a black-and-white camera. The light sources may be lasers. The wavelengths of the light sources may be selected from a group consisting of red, blue and green. The system may be expanded to more than two light sources.

A method to implement the time division illumination is also disclosed.

Additional aspects, alternatives and variations as would be apparent to persons of skill in the art are also disclosed herein and are specifically contemplated as included as part of the invention. The invention is set forth only in the claims as allowed by the patent office in this or related applications, and the following summary descriptions of certain examples are not in any way to limit, define or otherwise establish the scope of legal protection.

5.0 BRIEF DESCRIPTION OF THE DRAWINGS

The invention can be better understood with reference to the following figures. The components within the figures are not necessarily to scale, emphasis instead being placed on clearly illustrating example aspects of the invention. In the figures, like reference numerals designate corresponding parts throughout the different views and/or embodiments. It will be understood that certain components and details may not appear in the figures to assist in more clearly describing the invention.

FIG. 4 is a cross-sectional side view of the cuvette insert of FIG. 3, which illustrates the path of the electromagnetic light sheet.

FIG. 5 is a top view of the cuvette insert of FIG. 3 placed inside of a conventional cuvette.

FIG. 7 is a cross-sectional side view of an alternate embodiment of a cuvette insert that may be used.

FIG. 8 is a top view of the cuvette insert of FIG. 7 inside of a conventional cuvette.

FIG. 9 is an isometric view of the cuvette insert of FIG. 7 outside of a conventional cuvette.

FIG. 10 shows that the manufacturing of the cuvette insert of FIG. 7 can be accomplished by cutting, bending and welding or gluing thin sheets of a material such as aluminum.

FIG. 16A illustrates another embodiment of a cuvette insert.

FIG. 16B illustrates the insert of FIG. 16A with the interior channels shown.

FIG. 17A is a side schematic view of the insert of FIG. 16A.

FIG. 17B is a top schematic view of the insert of FIG. 16A.

Figure 21:
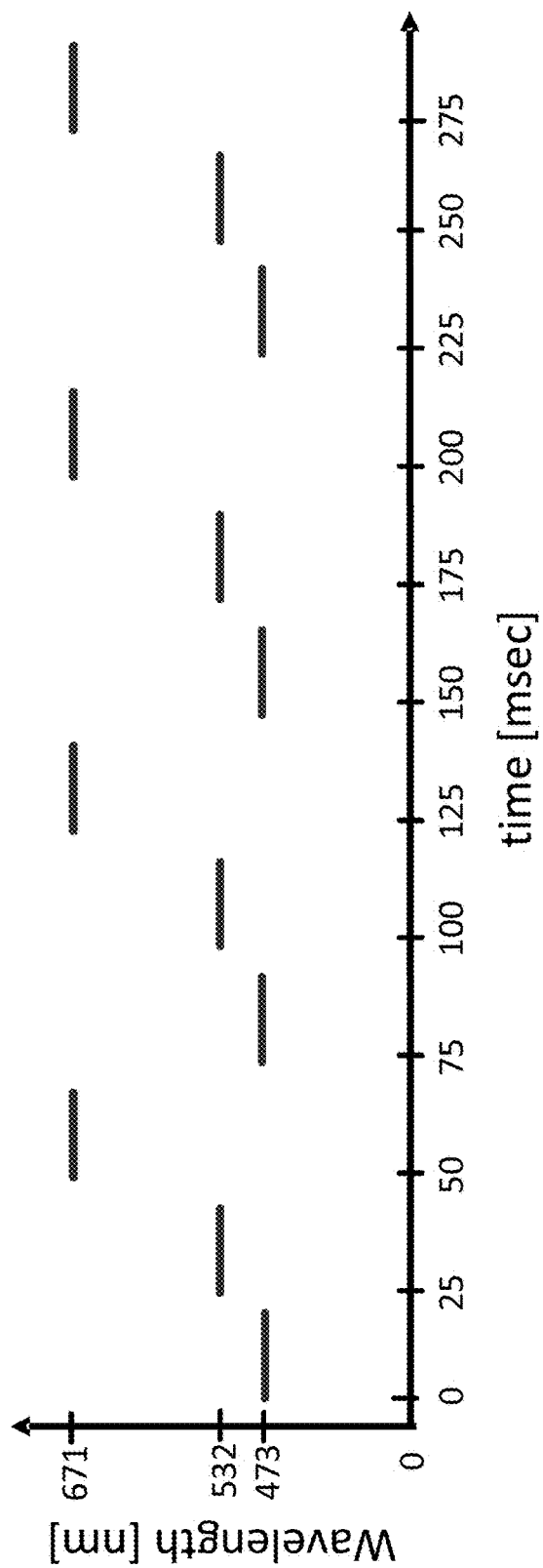

FIG. 21 graphically illustrates the illumination timing.

Figure 22:
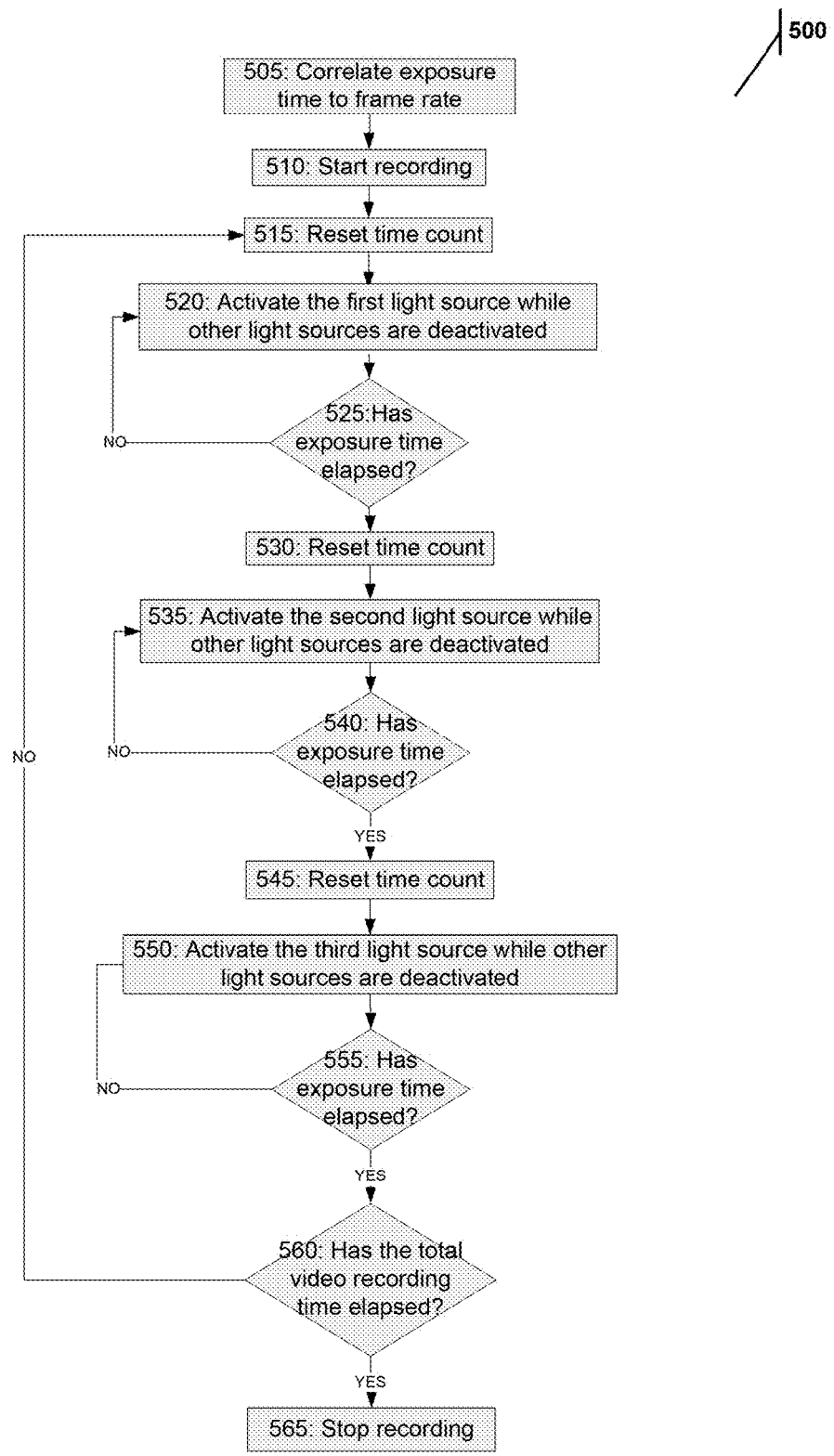

FIG. 22 illustrates a method to implement the time division illumination shown in FIG. 21.

Figure 23:
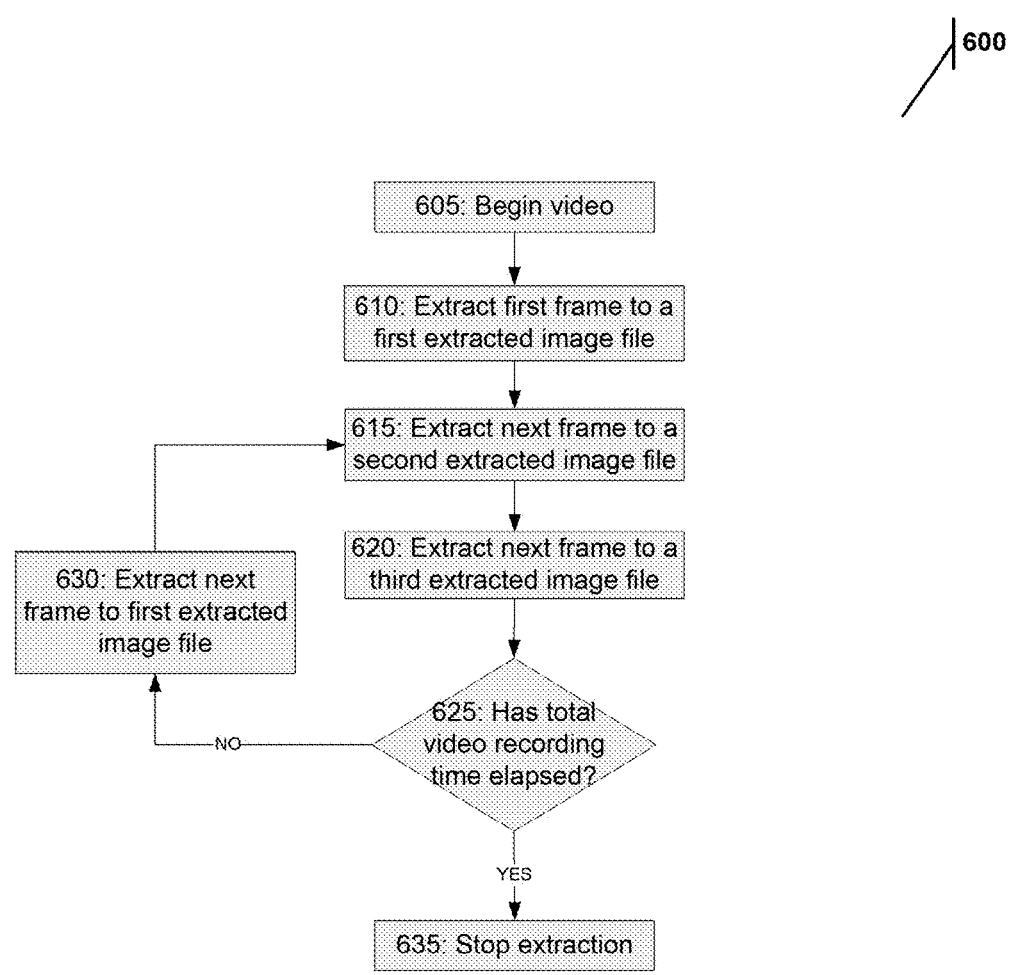

FIG. 23 illustrates a method of extracting video frames from a video that has recorded a video with time division illumination.

Figure 24:
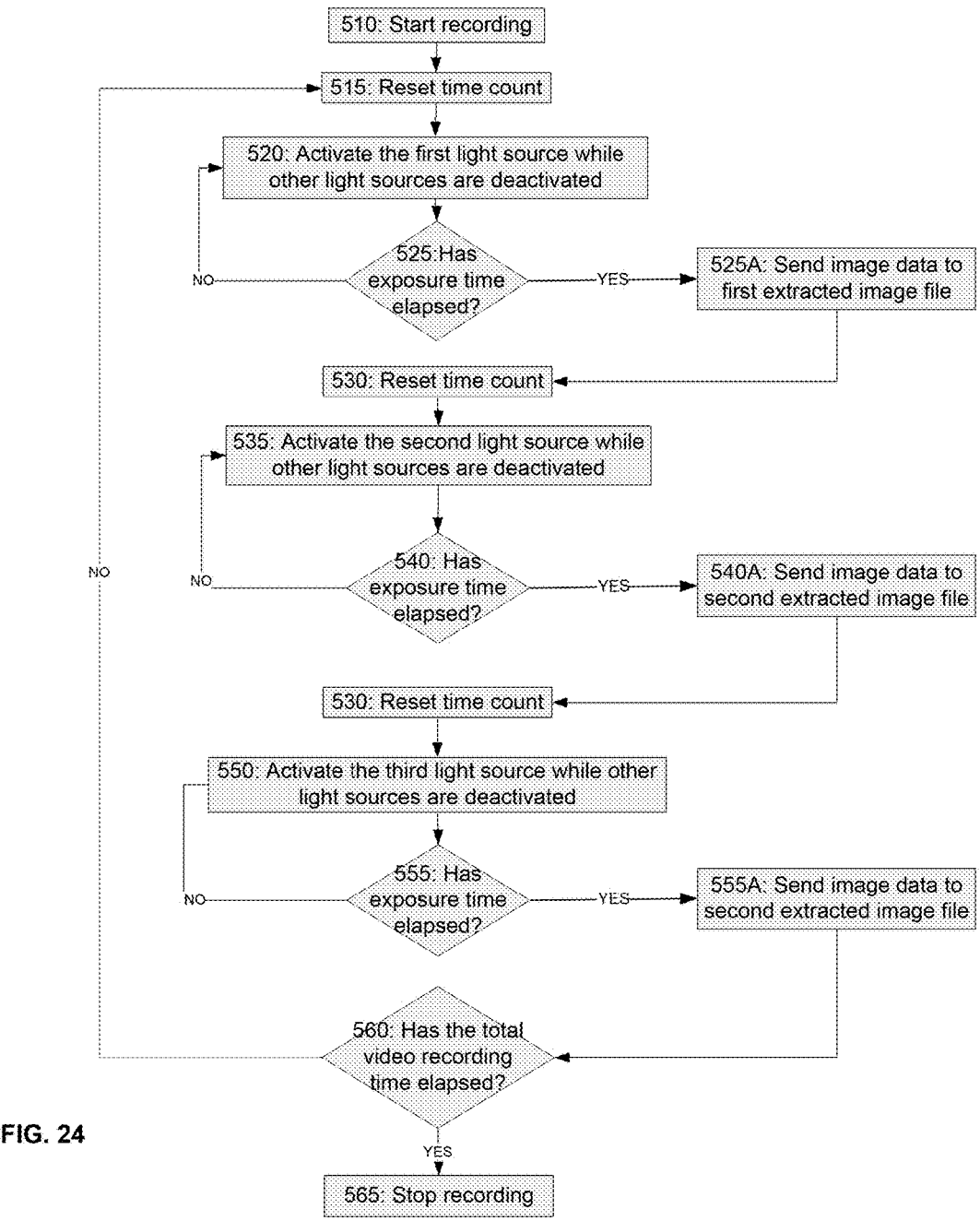

FIG. 24 illustrates a method to implement the time division illumination with integrated image extraction/segregation.

6.0 DETAILED DESCRIPTION

Reference is made herein to some specific examples of the present invention, including any best modes contemplated by the inventor for carrying out the invention. Examples of these specific embodiments are illustrated in the accompanying figures. While the invention is described in conjunction with these specific embodiments, it will be understood that it is not intended to limit the invention to the described or illustrated embodiments. To the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, process operations well known to persons of skill in the art have not been described in detail in order not to obscure unnecessarily the present invention. Various techniques and mechanisms of the present invention will sometimes be described in singular form for clarity. However, it should be noted that some embodiments include multiple iterations of a technique or multiple mechanisms unless noted otherwise. Similarly, various steps of the methods shown and described herein are not necessarily performed in the order indicated, or performed at all in certain embodiments. Accordingly, some implementations of the methods discussed herein may include more or fewer steps than those shown or described. Further, the techniques and mechanisms of the present invention will sometimes describe a connection, relationship or communication between two or more entities. It should be noted that a connection or relationship between entities does not necessarily mean a direct, unimpeded connection, as a variety of other entities or processes may reside or occur between any two entities. Consequently, an indicated connection does not necessarily mean a direct, unimpeded connection unless otherwise noted.

The following list of example features corresponds with FIGS. 1-23 and is provided for ease of reference, where like reference numerals designate corresponding features throughout the specification and figures:

a system for viewing nanoparticles 10
a light source 15
electromagnetic energy (beam or sheet) 20
a cuvette 25
an alternate embodiment of a cuvette 25A
a cuvette insert 28
an alternate embodiment of a cuvette insert 28A
a third alternative embodiment of a cuvette insert 28B
a cuvette holder 29
a sensor 30
cuvette exterior walls 35
cuvette floor 40
cuvette volume 45
backscatter reflection 47
transparent portion of cuvette exterior wall 50
viewing chamber 55
an upper viewing chamber wall 60
a lower viewing chamber wall 65
charged upper and lower viewing chamber wall 67+, 67−
non-reflective surface of upper and lower viewing chamber walls 68
vertical viewing chamber wall 69
a reflecting wall 70
highly-reflective surface of reflecting wall 72
opening from viewing chamber to backscatter chamber 74
a backscatter chamber 75
backscatter chamber walls 77
retention structure 78
fluid communication between backscatter chamber and viewing chamber 80
reflection of electromagnetic energy by the reflecting wall 85
mixing chamber 90
mixing chamber wall 93
fluid communication between mixing chamber and viewing chamber 95
mixing stick 100
lower quality portion of cuvette exterior wall 105
lifting block 110
radio tag 120
electrical isolation break between upper and lower viewing chamber walls 125
spacers 178
insert (2nd embodiment) 200
insert top surface 202
lifting eyelets 203
first vertical channel opening 205
second vertical channel opening 210
direction of the light sheet 215
direction of viewing 220
insert side wall 222
viewing chamber 225
upper viewing chamber wall 226
lower viewing chamber wall 228
reflecting wall 230
first vertical channel 235
second vertical channel 240
first lateral channel 245
second lateral channel/backscatter chamber 250
plug/topper 260
first vertical channel extension tube 265
second vertical channel extension tube 270
power source 275
cathode/first electrode 280
anode/second electrode 285
movement of colloidal particles 290
bubbles 295
depth of first vertical bore 300
depth of second vertical bore 305
direction of drilling for first and second vertical bores 310
depth of first lateral bore 315
depth of second lateral bore 320
direction of drilling for first and second lateral bores 325
direction of router to connect first and second lateral bores 330
a system for detecting electromagnetic radiation of multiple wavelengths 400
first light source at a first wave length 415 first beam of electromagnetic radiation at substantially a first wavelength 420
second light source at a second wavelength 425
second beam of electromagnetic radiation at substantially a second wavelength 430
combining structure/dichroic mirror 435
combined beam 440
light sheet former 445
specimen chamber/cuvette 450
a portion of the beam that scatters 455
imaging objective 460
sensor (camera) 465
processor 470
a method and steps to implement the time division illumination shown in FIG. 21 500-565
a method and steps of extracting video frames from a video that has recorded a video with time division illumination 600-635

The primary objective of the invention is to provide features inside a standard-sized cuvette that prevent or greatly limit liquid flow during recording of videos while still permitting the light sheet to enter the cuvette, and scattered light to exit the cuvette, while also allowing for stirring of the liquid inside the cuvette. The objective has been achieved through two parallel surfaces arranged so they straddle the incoming light sheet and enable recording of scattering light in a perpendicular direction. A second embodiment is to have only one surface that is parallel to the bottom of cuvette, with the base of the cuvette being lifted so the light beam enters between said surface and the bottom of cuvette. In the first embodiment, the surface closest to the bottom of the cuvette should have openings to permit stirring of the portion of the liquid between the two parallel surfaces. Additionally, an angled element placed in the path of the light sheet between the field of view of the video camera and the back wall of the cuvette prevents backscattering by reflecting the light sheet upwards and away from the field of view of the camera.

The manufacturing of these special-purpose cuvettes can be accomplished in at least two ways. One option is produce inserts (i.e., insert 28 shown in FIGS. 3-6; insert 28A shown in FIGS. 7-10; insert 28B shown in FIGS. 12-13) that are placed inside standard commercially-available glass cuvettes. Another option is to have the features molded into a cuvette that may be primarily made from plastic but with two optical glass windows molded into each of two sides of the cuvette 90 degrees apart. Such a construction may reduce costs by minimizing the use of expense materials such has optical grade glass. The following figures will more fully describe the innovation.

Figure 1:
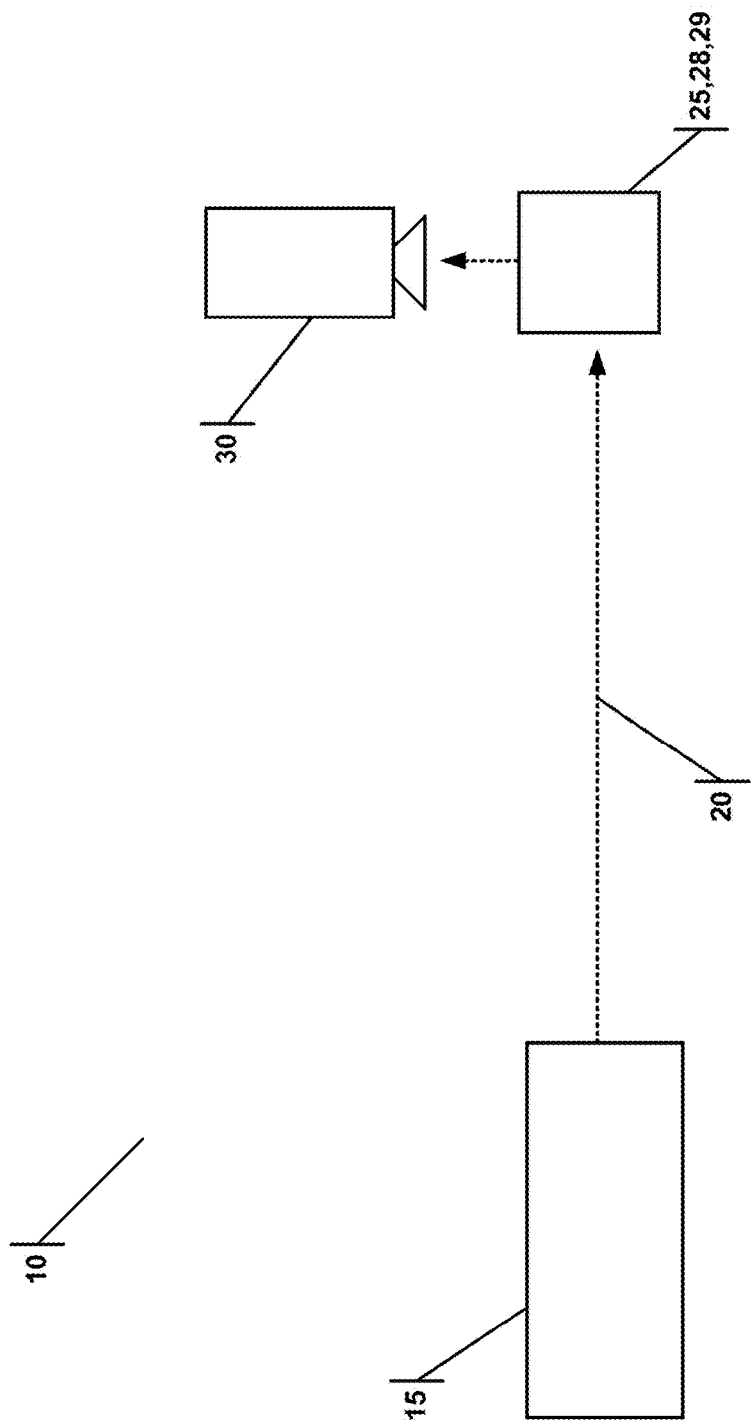
FIG. 1 illustrates a system for detecting nanoparticles using electromagnetic energy.

FIG. 1 illustrates a conventional laboratory setup with a system 10 to observe the Brownian movement of nanoparticles. A light source 15, generally a laser with associated optics (not shown) produces electromagnetic energy 20 (a light beam or sheet) that enters the cuvette 25. The cuvette 25 contains a liquid along with the nanoparticles. A sensor 30, which may include a microscope or camera (not shown), records the image from the cuvette 25, perpendicular to the direction of the electromagnetic energy 20. The cuvette 25 is held in place by a holder 29 that prevents movement of the cuvette to reduce motion-induced blurring and produce better images. According to the teachings of the present invention, the cuvette 25 may contain a cuvette insert 28 (shown in FIGS. 3-6) or insert 28A (shown in FIGS. 7-10) or insert 28B (shown in FIGS. 12-13), as discussed in detail below.

Figure 2:
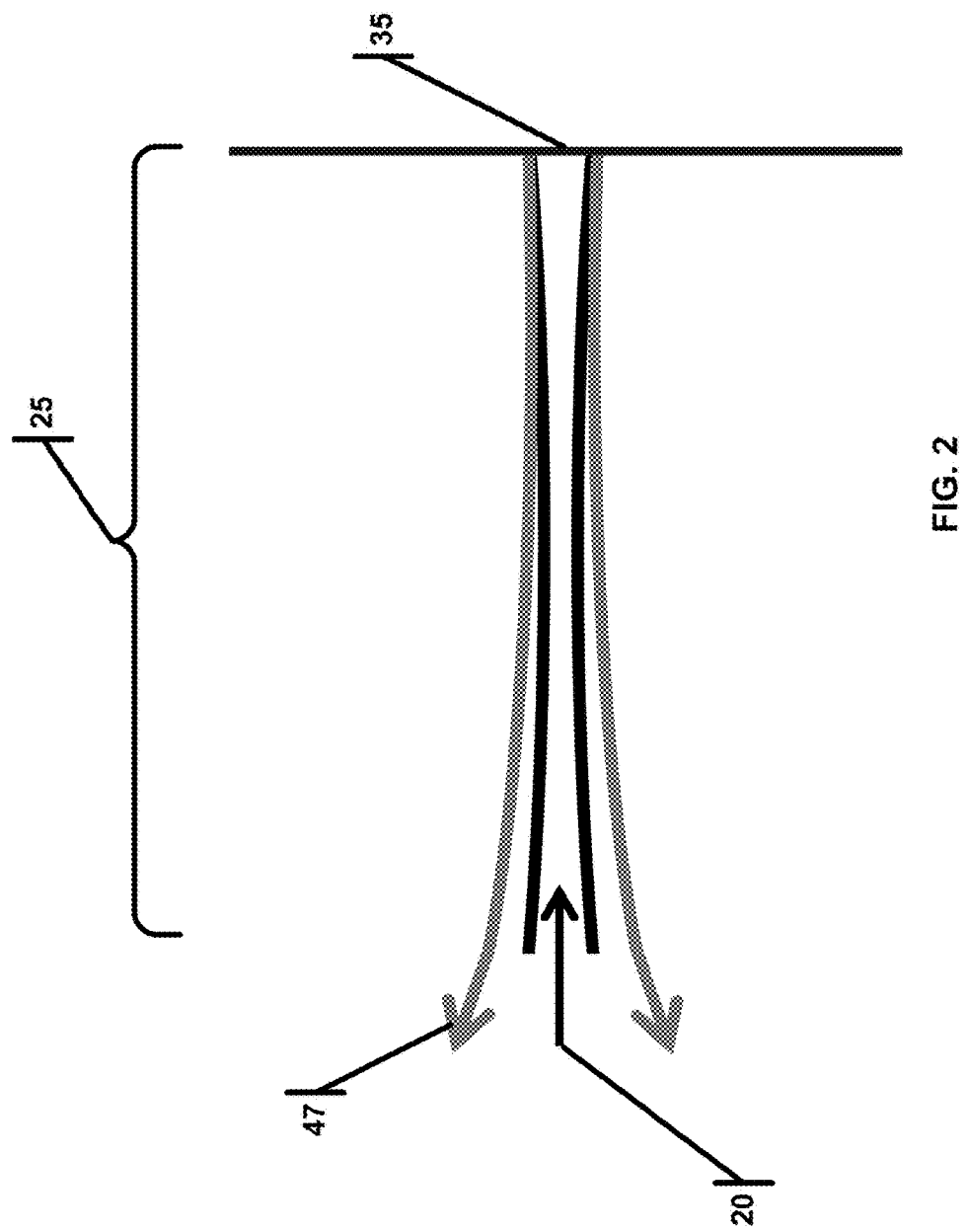
FIG. 2 illustrates the backscatter effect that causes blurry images and volume uncertainty.

FIG. 2 illustrates the backscatter effect that causes blurry images and volume uncertainty. The electromagnetic energy 20 enters the cuvette 25 and hits the cuvette exterior wall 35, causing the electromagnetic energy 20 to become less focused and thickened. This backscatter reflection is shown by arrows 47. When this less-focused light sheet hits the nanoparticles, the images captured by the sensor 30 may become blurred. While processing techniques exists to de-blur the images to some extent, the blurred images can and do lead to inaccurate analysis of Brownian motion.

Figure 3:
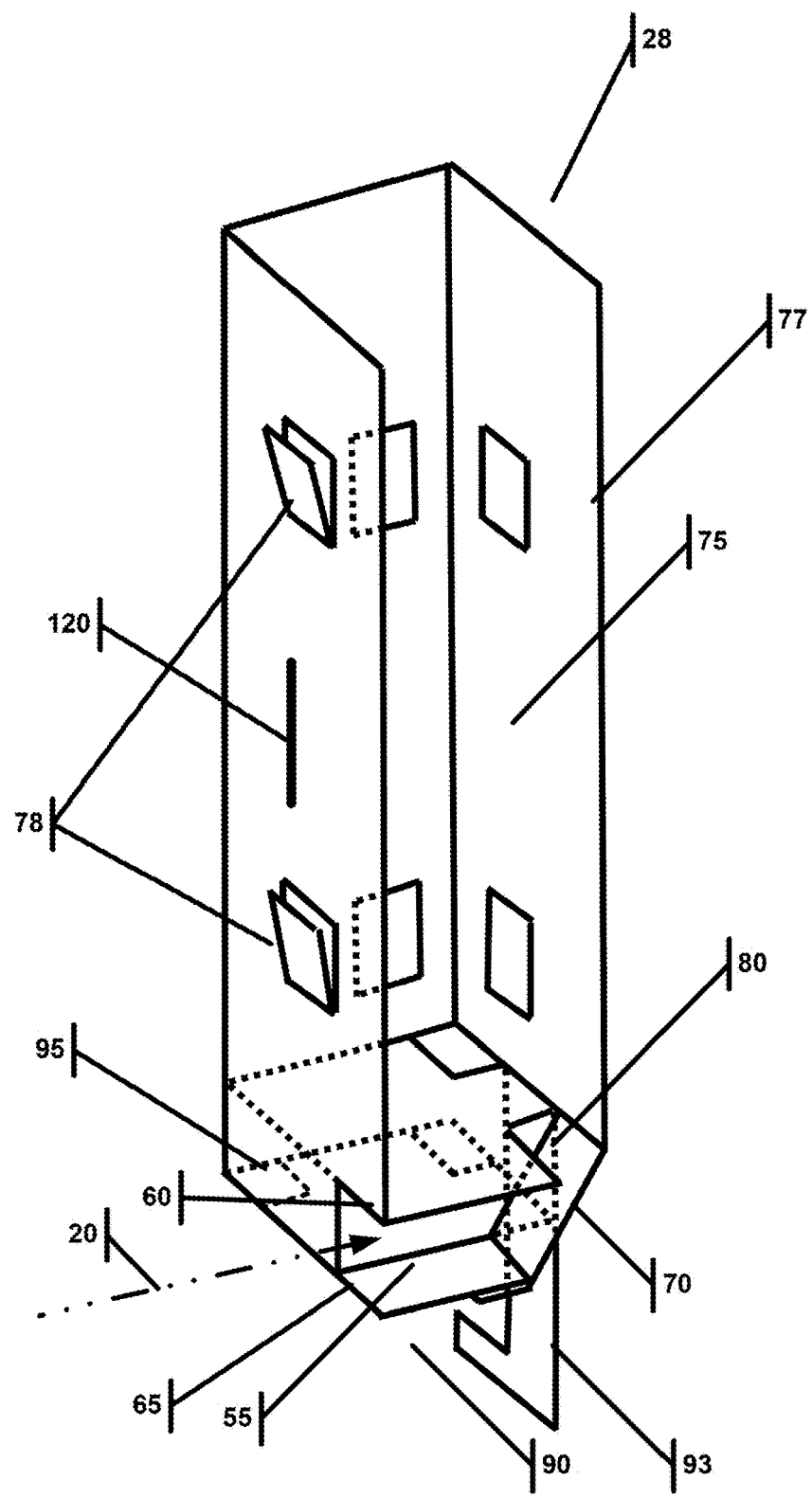
FIG. 3 is an isometric view of a cuvette insert that may be placed inside of a conventional cuvette.

FIG. 3 is an isometric view of a novel insert 28 that may be placed into a conventional cuvette 25 to overcome limitations of the standard design. The electromagnetic energy 20 enters the insert 28 as shown, passing through a viewing chamber 55 bounded by an upper viewing chamber wall 60 and a lower viewing chamber wall 65, and reflects at an angle off of a reflecting wall 70, entering a backscatter chamber 75. The angle may be between 30 and 60 degrees, optimally 45 degrees. The backscatter chamber 75 effectively prevents any backscatter from entering the viewing chamber 55. The sensor 30 can sense nanoparticles in the viewing chamber 55 in a direction that is perpendicular to the direction of travel of the electromagnetic energy 20. The reflecting wall 70 is highly reflective and angled so that the impinging electromagnetic energy 20 will be directed away from the viewing chamber 55 and into the backscatter chamber 75.

The insert 28 may also have one or more retention structures 78 in the backscatter chamber walls 77. The retention structures 78 extend away from the insert 28 and apply pressure to the cuvette to retain the insert 28 in place. These may be simple flaps as shown, or any other form of retention structure or adhesive as will be familiar to one skilled in the art.

The insert 28 may also include a mixing chamber wall 93 that elevates the insert 28 away from the bottom of the cuvette and, together with the lower portion of the cuvette, forms a mixing chamber 90. Fluid communication 95 between the mixing chamber and the viewing chamber and fluid communication 80 between the backscatter chamber 75 and the viewing chamber 55 allow the mixing motion to translate throughout the liquid within the insert 28. By increasing the thermal homogeneity of the liquid, this mixing motion minimizes thermally generated micro flows that can cause errant movement other than the desired Brownian motion. In an alternate use of the insert, the suspension liquid may fill substantially all of the viewing chamber 55, but the liquid does not fill the backscatter chamber 75. In such a use, the backscatter chamber 75 is still in fluid communication with the viewing chamber 55 and can still function to prevent deleterious backscatter of electromagnetic energy within the viewing chamber.

A radio tag 120, such as a radio-frequency identification (RFID) tag, may be attached to the cuvette insert 28 to monitor how many times it is used. RFID uses electromagnetic fields to automatically identify and track tags attached to objects, as is known in the art. The tag 120 contains electronically-stored information which is passed to a nearby reader (not shown) via a radio signal. The tag 120 may include, for example, a moisture sensor that detects the presence of a suspension liquid, such that each time the liquid is changed the sensor would register that change, indicating a separate use of the cuvette/insert.

FIG. 4 is a cross-sectional side view of the insert 28 which illustrates the path of the electromagnetic energy 20. The electromagnetic energy 20 reflects off of the reflecting wall 70 which has a highly reflective surface 72 and is angled away from a vertical viewing chamber wall 69, and then enters the backscatter chamber 75, which prevents the electromagnetic energy 20 from then reentering the viewing chamber 55 and causing blurred imagery or volume uncertainty. An arrow 85 shows reflection of electromagnetic energy by the reflection wall. The distance between the upper viewing chamber wall 60 and the lower viewing chamber wall 65 may be on the order of approximately 2 mm or another suitable dimension.

To further assist with reducing backscattering, upper and lower viewing chamber walls 60, 65 of the insert 28 may be painted black or have another non-reflective surface 68 applied. The sensor 30 would be placed perpendicular to the plane of the paper, and focused on the viewing chamber 55. Below the viewing chamber 55 and above the cuvette floor 40 is a mixing chamber 90 with a mixing stick 100 that is agitated by a magnet (not shown) outside of the cuvette 25.

The cuvette 25 may further be retained in the holder 29 by one or more spacers 178 in contact with the cuvette exterior walls 35.

FIG. 5 is a top view of the insert 28 inside of the cuvette 25. The mixing stick 100 is shown as a dashed line because it is below the viewing chamber walls 60, 65 of the insert, and cannot be seen from the top view. Fluid communication 80 between the backscatter chamber and the viewing chamber and fluid communication 95 between the mixing chamber and viewing chamber exist so that when the mixing stick 100 is agitated, that mixing motion translates throughout the cuvette volume 45. A dot 85 indicates reflection of the electromagnetic energy by the reflecting wall. For an exemplary cuvette with an outer dimension of 12.5 mm, a holder 13.3 mm in width would be appropriate, with spacers 178 retaining the cuvette 25 within the holder 29.

Figure 6:
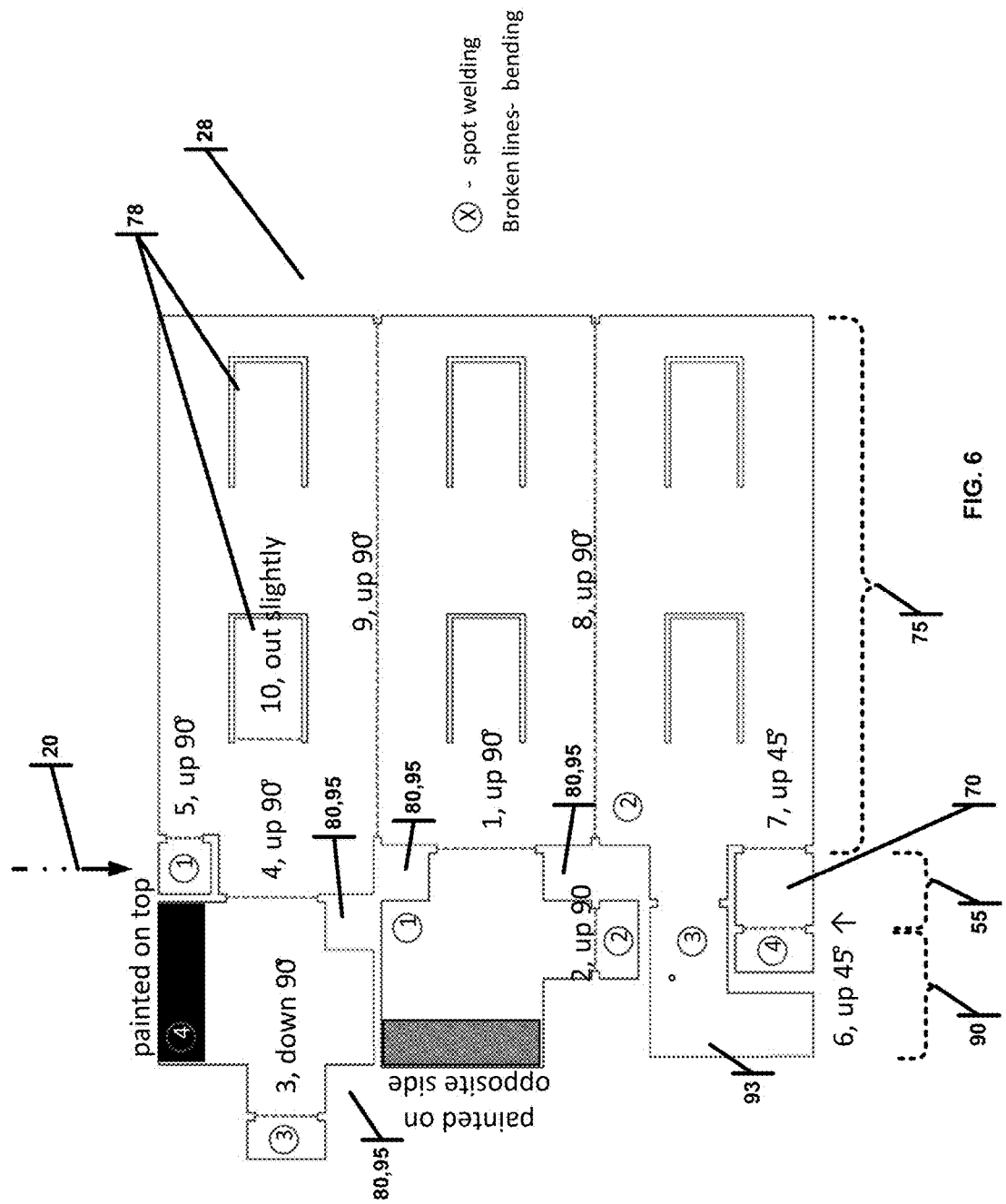
FIG. 6 shows that the manufacturing of the cuvette insert of FIG. 3 can be accomplished by cutting, bending and welding or gluing thin sheets of a material such as aluminum.

FIG. 6 shows that the manufacturing of the insert 28 can be accomplished by cutting, bending and welding or gluing thin sheets of a material such as aluminum. Cutting and bending a sheet according to FIG. 6 results in the insert shown in FIG. 3. The sheet metal is cut as shown. Broken lines indicate bending locations, while spot welds are to be made at the points indicated. Two tab ends are painted as marked to provide the non-reflective surface of the viewing chamber walls 68. In steps (1) and (2), the opposite-side partially painted tab and its attached smaller tab are bent up 90°. At steps (3), (4), and (5), the partially painted-on-top tab is bent down 90°, its attached smaller tab is bent up 90°, and an adjacent small tab is bent up 90°. In steps (6) and (7), small tabs which will form the reflecting wall 70 are bent up 45°. At steps (8) and (9), the backscatter chamber walls are bent up 90°. Step (10) is to pull the tabs of the retention structure 78 out slightly. Alternatively, or additionally, the cuvette can be chemically bonded to the insert to make an integrated cuvette/insert assembly.

FIG. 7 is a cross-sectional side view of an alternate embodiment of a cuvette insert 28A that may be used. The insert allows the electromagnetic energy 20 to enter and exit the cuvette 25. The upper viewing chamber wall 60 may be painted black or have another non-reflective surface applied. Unlike the previously disclosed embodiment, the viewing chamber 55 and the mixing chamber 90 are one and the same, and the floor of the cuvette 40 doubles as the lower viewing chamber wall 65. The insert 28A may also include a vertical-viewing chamber wall 69 that elevates the insert away from the bottom of the cuvette 25 and creates the viewing/mixing chamber 55, 90. The cuvette 25 may be raised within the holder 29 by a lifting block 110 having dimensions of, for example, 11 mm by 11 mm by 6.25 mm. The cuvette 25 may have a typical thickness of 1.25 mm, and the viewing/mixing chamber 55, 90 may be 2 mm in height. The electromagnetic energy 20 would then enter the cuvette 25 at a height of 8.5 mm.

FIG. 8 is a top view of the insert 28A inside of the cuvette 25. The mixing stick 100 is shown as a dashed line because it is below the upper viewing chamber wall 60, and cannot be seen from the top view. Fluid communication 80 between the backscatter chamber and the viewing chamber and fluid communication 95 between the mixing chamber and viewing chamber exist so that when the mixing stick 100 is agitated, that mixing motion translates to the cuvette volume 45. A dot 85 indicates reflection of the electromagnetic energy by the reflecting wall. For an exemplary cuvette with an outer dimension of 12.5 mm, a holder 13.3 mm in width would be appropriate.

FIG. 9 is an isometric view of the insert 28A that may be placed into a conventional cuvette 25. The insert 28 may also have retention structures 78 that extend away from the insert and apply pressure to the cuvette 25 to retain the insert 28 in place. An opening 74 from the viewing chamber to the backscatter chamber enables fluid communication and passage of electromagnetic energy. A radio tag 120 may be attached to the cuvette insert 28A for asset-monitoring purposes, as discussed above.

FIG. 10 shows that the manufacturing of the insert 28A can be accomplished by cutting, bending and welding or gluing thin sheets of a material such as aluminum. Cutting and bending a sheet according to FIG. 10 results in the insert shown in FIG. 9. The sheet metal is cut as shown. Broken lines indicate bending locations, while spot welds are to be made at the points indicated. A tab end is painted as marked to provide the non-reflective surface of the viewing chamber walls 68. In steps (1) and (2), the opposite-side partially painted tab and its attached smaller tab are bent up 90°. At step (3) a small tab which will form the reflecting wall 70 is bent up 45°. At step (4), the backscatter chamber walls are bent up 90°. Step (5) is to pull the tabs of the retention structure 78 out slightly.

Figure 11:
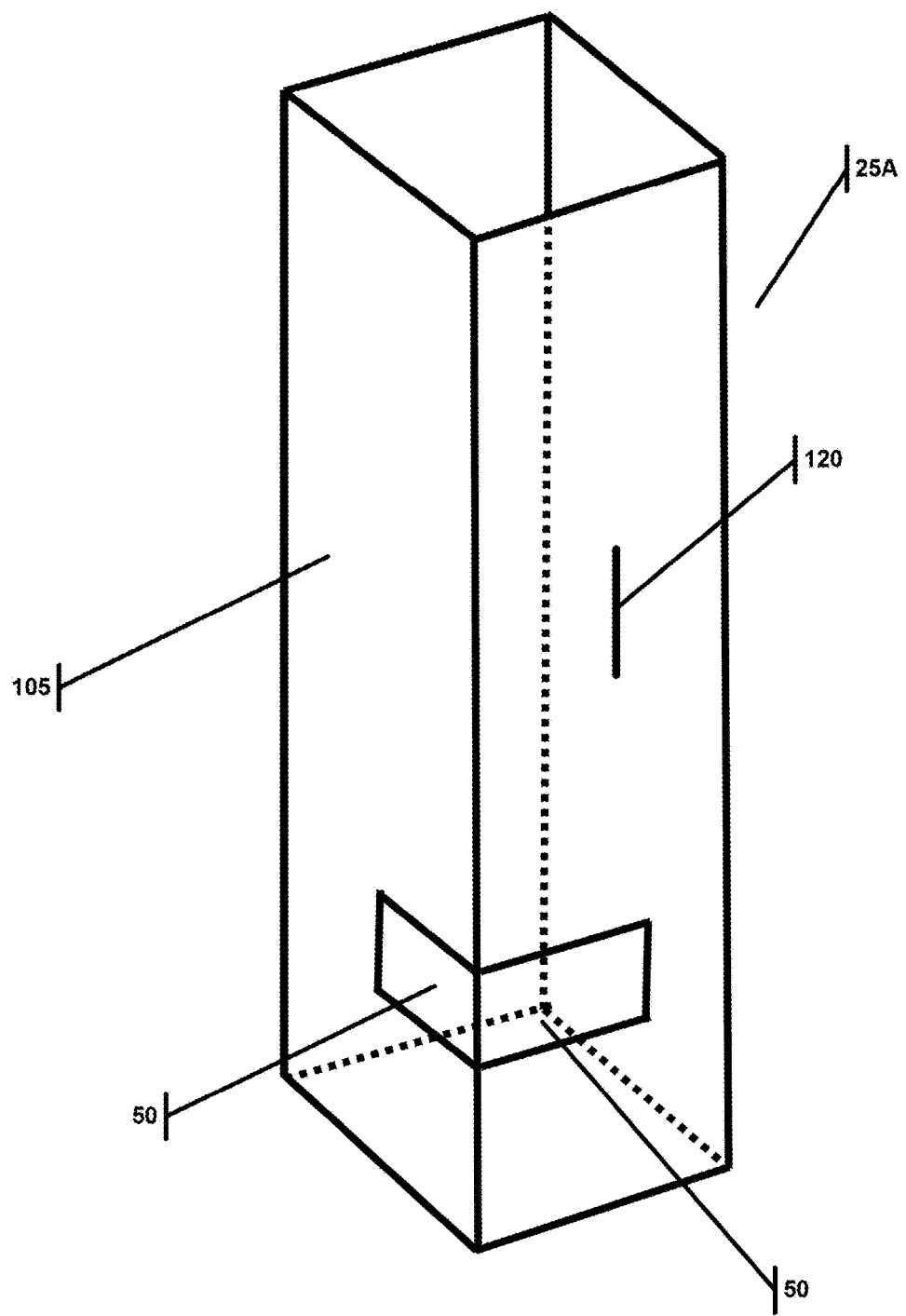
FIG. 11 illustrates a novel cuvette manufactured with different materials to save on cost.

FIG. 11 shows a novel cuvette 25A that may be used with the inserts described herein. Cuvettes are generally made of high-quality glass and thus can be extremely expensive. The cuvette 25A is primarily made of a less expensive plastic. The cuvette exterior wall has a main lower-quality portion 105 with smaller transparent portions 50 where the light sheet enters and the sensor 30 views the nanoparticles. These portions 50 are made of high-quality glass, minimizing backscatter and other optically deleterious effects. When the insert 28A (FIGS. 7-10) is used, the cuvette 25A may also include a region that allows the light sheet to exit the cuvette 25A, minimizing backscatter. A radio tag 120 may be attached to or imbedded in the cuvette 25A for asset-monitoring purposes, as discussed above.

Figure 12:
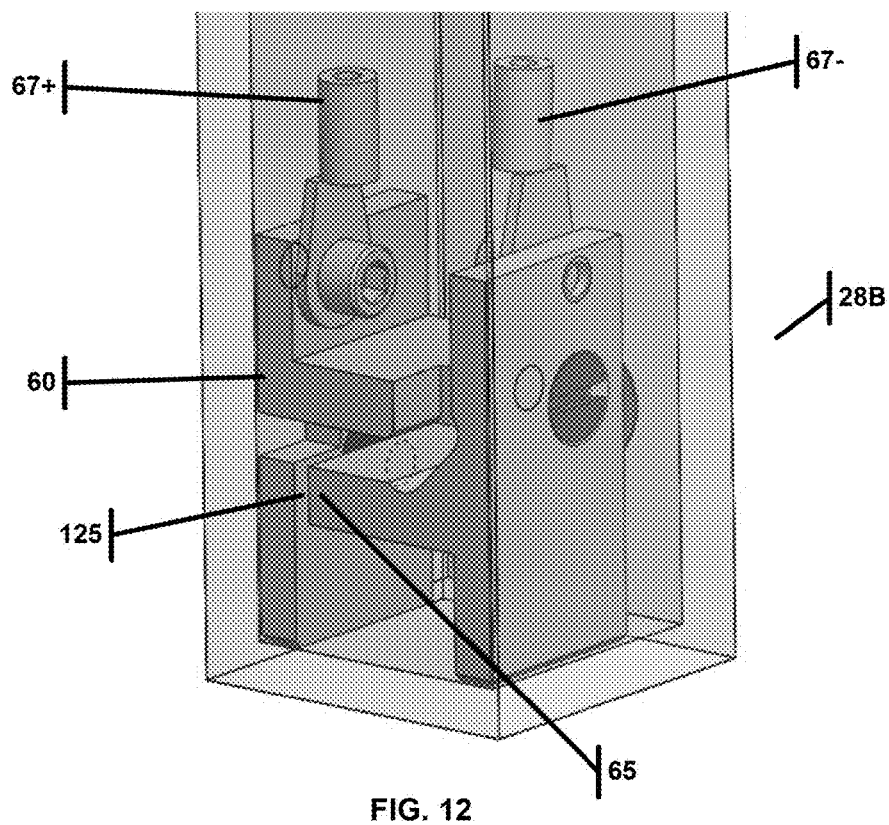
FIG. 12 is an isometric view of an alternate embodiment of a cuvette insert that may be used to create an electric field within the viewing chamber.
Figure 13:
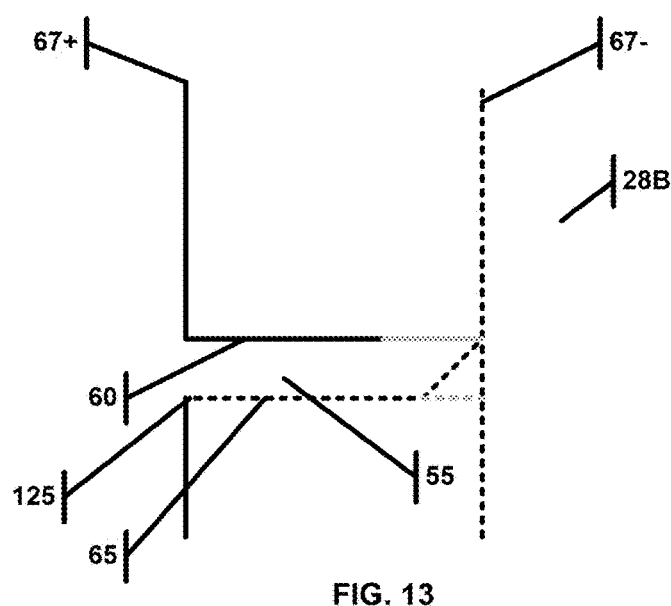
FIG. 13 is a cross-sectional side view of the cuvette insert of FIG. 12, which illustrates the electrical isolation between the upper and lower viewing chamber walls.

Referring to FIGS. 12 and 13, an insert 28B is disclosed that may be used to determine the zeta-potential of the nanoparticles. The upper and lower viewing chamber walls 60, 65 may be electrically charged 67+, 67− to create an electromagnetic field within the viewing chamber 55. The upper viewing-chamber wall 60 is electrically isolated from the lower viewing chamber wall 65 as shown in FIG. 12 where there is a break in the conduct material between the upper and lower viewing chamber walls 60,65 (shown at position 125). FIG. 13 illustrates this construction where the upper viewing chamber wall 60 is in electric conductivity with the portion of the insert 28C shown as a solid line. Another portion of the insert 28B is in electrical conductivity with the lower viewing chamber wall 65 (shown as a dashed line), where the break 125 electrically isolates the upper and lower viewing chamber walls 60,65 from each other. When electric potential is being applied to two parallel surfaces of the insert 28B, the presence of an electric field across the colloid forces particles that are forming the colloid to move toward the electrode of opposite charge to the charge that is present on each particle (the so-called zeta-potential or layer of charge on the interface between the particle surface and the liquid in which it is immersed). By tracking the speed of movement of each particle versus the applied electric field (when light is being introduced into cuvette, scattered on the particles of the colloid and then recorded by the camera as a time series of images), one can estimate the value of zeta-potential using electrophoresis theory of M. Smoluchowski (1903) "Contribution à la théorie de l'endosmose électrique et de quelques phénomènes corrélatifs", Bull. Int. Acad. Sci. Cracovie, 182-199, the contents of which are incorporated herein by reference. The configuration of the electric field perpendicular to the direction of light illumination and perpendicular to the direction of observation allows for easy estimation of the speed of the particles induced by the electric field; the speed is equal to the distance travelled in time divided by that time, and both are easily measurable between two positions of any particle tracked in video recorded during measurement.

FIGS. 16A-19 illustrate yet another embodiment. As with the embodiments above, the structure can be a standalone insert that is used with a conventional cuvette or the features may be formed as an integral part of a cuvette. Turning now to FIGS. 16A and B, the insert 200 has a top surface 202 that includes a first and second vertical channel opening (205, 210). A first vertical channel 235 extends downwardly from the first vertical channel opening 205 and a second vertical channel 240 extending from the second vertical channel opening 210. The insert 200 also has a side wall 222 into which the viewing chamber 225 is formed. The viewing chamber 225 has an upper viewing chamber wall 226 and a lower viewing chamber wall 228. These walls define the viewing chamber 225 and may be substantially parallel to the floor of the cuvette into which the insert 200 is inserted. At the end of the viewing chamber is a reflecting wall 230 (discussed in detail above). The viewing chamber 225 has two ends, with one end in fluid connection with the first vertical channel and the other end in fluid connection with the second vertical channel. The fluid connection between the viewing chamber 225 and the first vertical channel 235 may also include a first lateral channel 245. Likewise the fluid connection between the viewing chamber 225 and the second vertical channel 240 may include a second lateral channel 250. The top surface 202 may also have a lifting eyelet 203, so make insert and removal of the insert 200 into and out of the cuvette easier.

As with the embodiments already described, the reflecting wall may be made of a reflecting material and may form an angle with the lower viewing chamber wall. This angle may be between 30 and 60 degrees. To help minimize scattering the upper and lower viewing chamber (226, 228) may have a very-low reflective or a non-reflective surface.

FIGS. 17A and B show the side and top view, respectively, of the insert 200 used in a cuvette 25. Arrow 225 illustrates the direction of the light sheet which is reflected by the reflecting wall 230. When the inset 200 is inserted into a cuvette 25 a topper or plug 260 may be used to maintain the insert 200 in a stable viewing position. To provide viewing chamber 225 access to the suspension liquid and particles, first and second vertical channel extension tubes (265, 270) may be implemented that exit the topper/plug 260. The user of the insert 200, therefore easily may introduce new material into the viewing chamber 225. FIG. 17B is a top view and illustrates the direction of viewing 220 of the viewing chamber 225.

Figure 18:
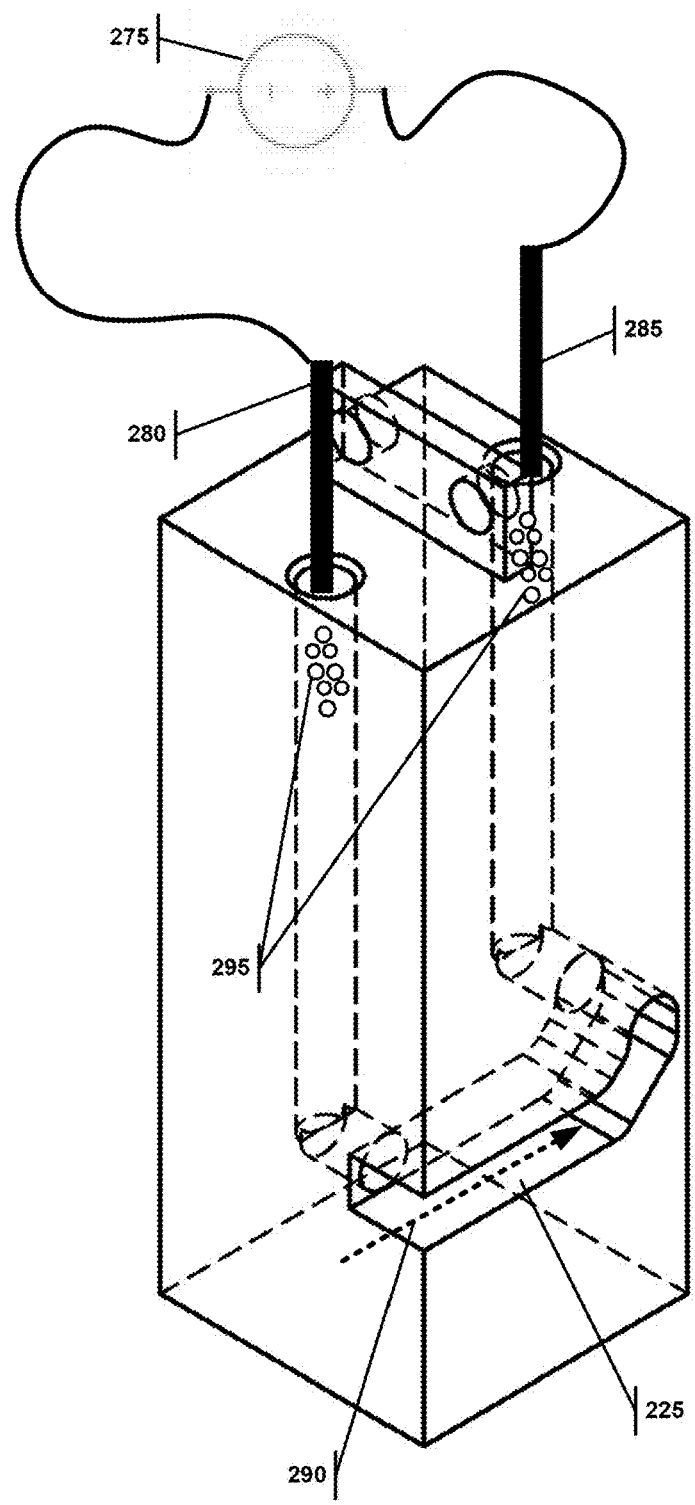
FIG. 18 is a perspective view of the insert of FIG. 16A with electrodes connected to measure the zeta-potential of the nanoparticles.

FIG. 18 illustrates the insert 200 used with a first and second electrode (280, 285). As discussed above, applying an electric potential across these electrodes (280, 285) by the power source 275 forms an electric field shown as arrow 290 (which may be in a reverse direction depending on the charge of the particles experiencing the field) and the particles in the colloid will move toward the electrode of opposite charge to the charge that is present on each particle (the zeta-potential or layer of charge on the interface between the particle surface and the liquid in which it is immersed). By tracking the speed of movement of each particle versus the applied electric field (when light is being introduced into cuvette, scattered on the particles of the colloid and then recorded by the camera as a time series of images), one can estimate the value of zeta-potential using electrophoresis theory of M. Smoluchowski (1903) "Contribution a la théorie de l'endosmose électrique et de quelques phénomènes corrélatifs", Bull. Int. Acad. Sci. Cracovie, 182-199, the contents of which are incorporated herein by reference. It should be noted that while a preferred construction of the insert is made from aluminum, the aluminum may have an aluminum oxide outer layer that is not electrically conductive, such that use of the electrodes previously described will not electrically short.

The insert 200 has an advantage over the insert shown in FIGS. 12 and 13, in that any bubbles 295 that are formed on the electrode will not be observed in the viewing chamber 225. Instead, given the construction of the first and second vertical channels (235, 240) the bubbles 295 will float away from the viewing chamber 225 and can be collected and gassed-off; thus preventing them from reaching the viewing chamber 225 and interfering with the observation of particle movement.

From these drawings, it is clear that the first and second channel openings (205, 210) are in fluid communication with each other according to the following route: first vertical channel opening 205→first vertical channel 235→first lateral channel 245→viewing chamber 225→second lateral channel 250→second vertical channel 240→second vertical channel opening 210. In an alternative, the lateral channels (245, 250) may not be necessary if the viewing chamber is sufficiently deep to reach the first and second vertical channels (235, 240). In other words, the first and second vertical channels (245, 250) would connect directly to the viewing chamber 225.

Figure 19:
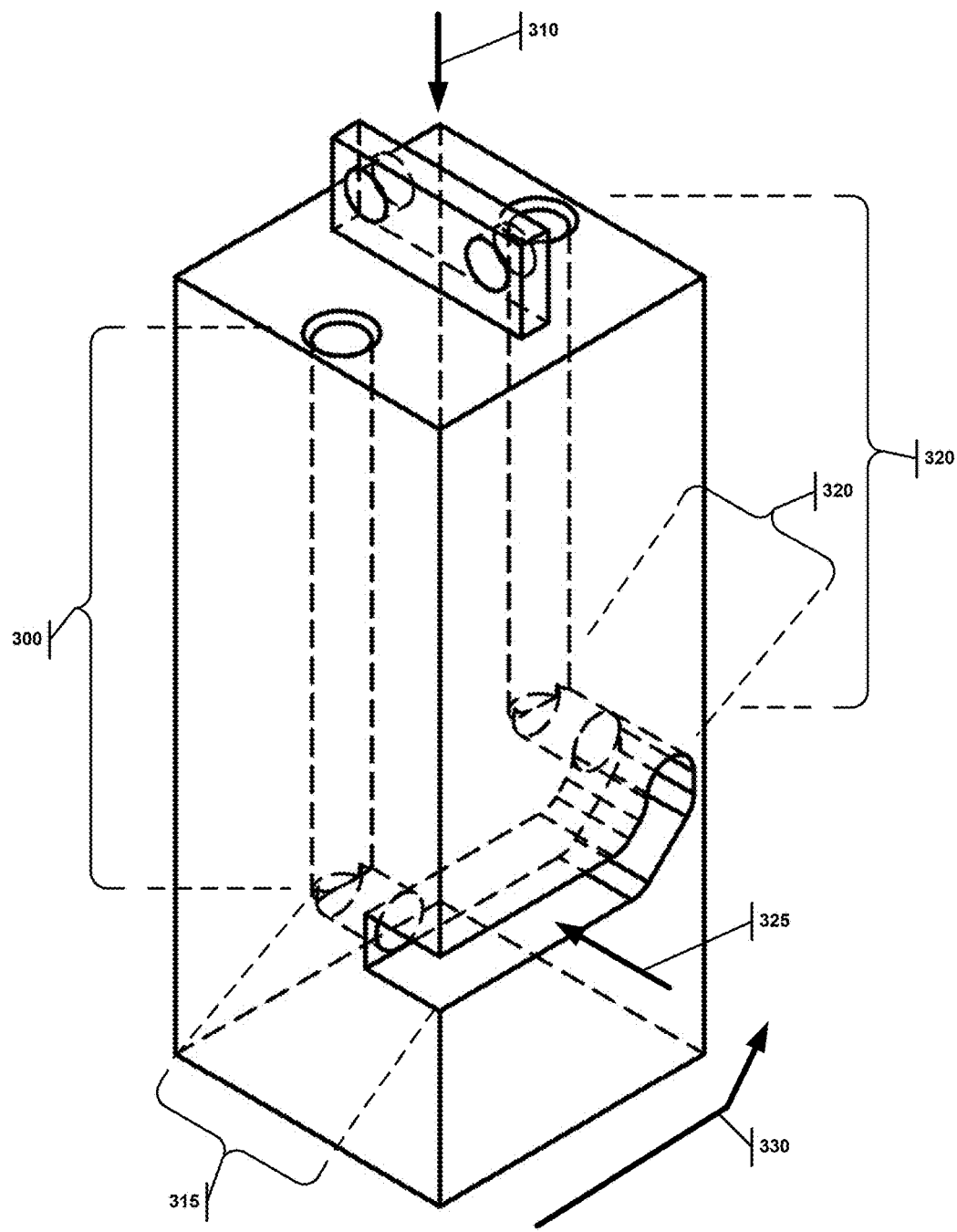
FIG. 19 illustrates a method of manufacture for the insert of FIG. 16A.

Turning now to FIG. 19, a method of manufacture is shown. The insert 200 may be manufactured from a block of aluminum or other uniform material. Once the block is formed into the outer rectangular dimensions, the first vertical channel made be drilled from the top (direction of arrow 310) to a depth of the first vertical bore 300. Likewise the second vertical channel may be drilled to a depth of the second vertical bore 305. The first lateral channel may be drilled from the side (direction of arrow 325) to a depth of the first lateral bore 315. Likewise the second lateral channel may be drilled to a depth of the second lateral bore 320. A router may be used to from the viewing chamber by routing a connection between the first lateral bore and the second lateral bore in the direction of arrow 330. In a variation, the lateral channels (245, 250) may not be necessary if the viewing chamber 225 is routed sufficiently deep to reach the first and second vertical channels (235, 240). In other words, the first and second vertical channels (235, 240) would connect directly to the viewing chamber 225.

Now, a novel method of recording multicolored light scattered on nanoparticles is described. Previous patent applications U.S. patent application Ser. No. 14/730,138, filed on Jun. 3, 2015, titled "NANOPARTICLE ANALYZER," and U.S. patent application Ser. No. 15/018,532 filed on Feb. 8, 2016, titled "MULTI-CAMERA APPARATUS FOR OBSERVATION OF MICROSCOPIC MOVEMENTS AND COUNTING OF PARTICLES IN COLLOIDS AND ITS CALIBRATION" disclose methods for recording of nanoparticle Brownian motion using single color camera or multiple B/W cameras using multiple colored light sheets. These applications are incorporated herein by reference.

Those disclosures can be extended by using single camera, preferably a B/W camera, and the same multi-colored laser sheet that was already described. The light sheet is prepared in the same way as in previous applications, i.e. two or more laser beams of different wavelengths are combined using dichroic mirrors into a single, multicolored beam that is compressed into a light sheet by a cylindrical lens and then compressed even more by an objective. (See e.g. FIGS. 3A and 3B of U.S. patent application Ser. No. 15/018,532; FIG. 1 of U.S. patent application Ser. No. 14/730,138; and the accompanying disclosure thereof). The focused multicolored light sheet illuminates nanoparticle colloid contained in a cuvette that may be equipped with an insert that prevents convection motion of a liquid. This insert may be made according to the disclosure herein. The light scattered by nanoparticles contained in a colloid is observed by a microscope at usually (but not necessarily) at a 90-degree angle relative to the light sheet plane. It should be noted that the angle of observation need not be 90-degrees; what is important is that the scatter light is observed. The scattered light is recorded as a video on a digital camera. Subsequently the video is processed so tracks created by the scattered light can be used to size nanoparticles using the Einstein equation (Einstein 1905 Annalen der Physik, 17, 549-560 "Über die von der molekularkinetischen Theorie der Wärme geforderte Bewegung von in ruhenden Flüssigkeiten suspendierten Teilchen").

Figure 20:
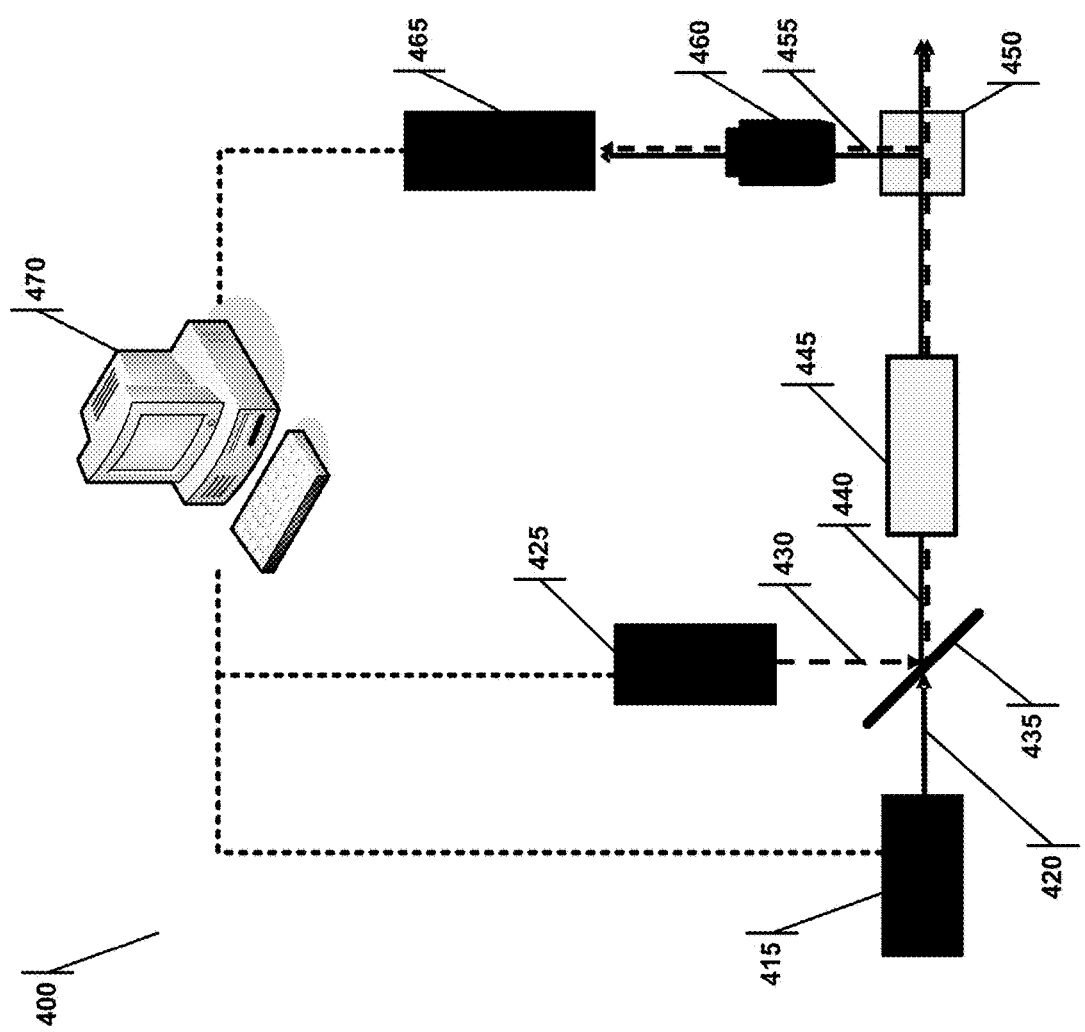
FIG. 20 illustrates a system for detecting electromagnetic radiation of multiple wavelengths that may be used with a time division illumination.

FIG. 20 illustrates an apparatus 400 for detecting electromagnetic radiation of multiple wavelengths may comprise a first light source at a first wave length 415 and a second light source at a second wavelength 425, such as two lasers with different beam colors or wavelengths. Each of these two beams is directed at a combining structure 435, such as a dichroic mirror, which combines the beams from light sources 415, 425 into a single combined beam 440 and directs the combined beam 440 to an optical system such as a light sheet former 445. The light sheet former 445 may comprise a cylindrical lens with long working distance objective that forms a very narrow sheet of illumination. The light sheet may be directed to a transparent specimen chamber 450 (such as a cuvette) that houses a colloid containing particles, i.e. nanoparticles (not shown). A portion of the combined beam that scatters 455 upon impacting the particles present in the colloid solution contained within the cuvette 450 has the same wavelengths as the illuminating light from the light sheet former 445, and can typically be observed at 90-degree angle by focusing an imaging objective 460, such as a microscope equipped with another long working distance objective. The scattered light exiting the imaging objective 460 may continue to a sensor such as a camera 465. A processor 470 may be connected to the first light source 415 and second light source 425 to implement a time division illumination schema discussed below. The processor 470 may also be connected to the sensor so as to extract multiple video streams from a video that has recorded a video with time division illumination, as described below.

In this novel method, each laser beam is pulsed in synchronization with recording camera forming a sequence of pulses with different colors activated during each frame. For example, if a B/W camera is set for 40 frames per second, i.e. time distance between frames is 25 milliseconds, and three different colors of lasers (red 671 nm, green 532 nm, blue 473 nm) are used to form the laser sheet, then first blue laser is activated at start time point of 0 seconds for less than 25 milliseconds, second green laser is activated at time point of 25 milliseconds for less than 25 milliseconds and third red laser is activated at time point of 50 milliseconds for less than 25 milliseconds. Then the sequence repeats, i.e. first blue laser is activated at time point of 75 milliseconds, the second green laser at time point of 100 milliseconds and the third red laser at time point of 125 milliseconds and so on as depicted in FIG. 21 schematically. Hence the camera will record series of B/W or greyscale images that in a sequence will correspond to illumination from the first blue laser, then the second green laser and, the third red laser, and so on. While pulsing is the preferred embodiment, the system may include a shutter system that obstructs the beam from reaching the specimen chamber, and therefore reaching the sensor. The shutters can be constructed such that only one beam illuminates the specimen chamber at a time.

It should also be noted that while the lasers may be combined when they are illuminated simultaneously, when the lasers are individually pulsated there is no such combined beam. The use of the combining structure 435, such as a dichroic mirror, and the light sheet former 445 ensure that each laser illuminates the specimen chamber from the same direction and position. The only difference experienced by the particles therefore is the wavelength of the illumination. The particles, depending on their size and material, would scatter and absorb the wavelengths differently.

To separate tracking at different colors, the processor chooses frames one, fourth, seventh etc. for laser one, frames second, fifth, eight etc. for laser two and frames third, sixth, ninth etc. for third laser. By picking up these sequences of frames from the original video, the processor effectively creates three different videos, each corresponding to different laser color and with three times smaller frame rate per second than originally recorded video (13.33 fps in the example used above). The following processing of these videos is similar to that described in the previous patent applications. This method can be applied to two lasers used as well as more than three. And this method is also applicable to record photoluminescence of colloidal particles.

FIG. 22 illustrates a method 500 to implement the time division illumination shown in FIG. 21. The first step (505) is to correlate the exposure time to the frame rate. In the example given above, the frame rate was 40FPS, so the exposure time was 25 milliseconds. It is also possible to set the exposure time for multiple frames—i.e., it could be set for 50 milliseconds. It is further possible to have a variable exposure time which may be helpful if the light source at a particular wavelength is fainter. So, for example, the exposure time for blue and green lasers might be a single frame (i.e., 25 ms in the example above) and the exposure time for the red laser might be two frames (i.e., 50 ms). Whatever the exposure time correlation to the frame rate, this same scheme should be used in the extraction method 500 discussed below.

Returning to the method 500 (which assumes a non-variable exposure time of a single frame), at step 510 the camera recording is started and the time count is reset to zero (Step 515). The first light source is activated (step 520) for the exposure time (step 525). Then the second light source is activated (step 535) for the exposure time (step 540). Then the third light source is activated (step 550) for the exposure time (step 555). This process is serially repeated until the total video recording time has elapsed (step 560) and the recording is stopped (step 565). It should be noted that the total recording time need not be set a priori; rather steps 560 and 565 may simply be the operator allowing the system to continue recording until the operator stops the recording. Also the system may be simplified with only two light sources (thus steps 450 and 555 could be deleted), or additional light sources may be added such that additional nested routine (e.g. steps 550 and 555) could be included to accommodate the additional light sources.

FIG. 23 illustrates a method 600 of extracting video frames from a video that has recorded a video with time division illumination. First, the recording is started at step 605 and the first frame is extracted to a first extracted image file (step 610). The next frame is extracted to a second extracted image file (step 615) and the next frame is extracted to a third extracted image file. If the total video recording time has not elapsed (step 625) then the next frame is extracted to first extracted image file (step 630) and the process continues to step 615. Once the video recording time has elapsed, the extraction may be stopped (step 635). Again, the operator may stop the extraction at any time. In the described method 600, the extraction assumed an exposure time that matched a single frame. If however, the exposure time correlated to two frames, then the extraction method 600 would need to account for this and extract two successive frames and assign to each image file. Similarly, if the exposure time were variable, the extraction method 600 would need to track the exposure scheme when creating the various video streams.

The extraction process may also be performed at the time the image data is obtained from the sensor. This is shown in FIG. 24, which is similar to the time division illumination method of FIG. 22, with the addition of steps 525A, 540A and 555A which automatically extract the images to the segregated extracted image files.

6.1 Results

In multiple tests on prototypes and commercial implementations of the cuvette/insert disclosed herein, the following have been shown. First, all backscatter from the cuvette wall opposite from the wall where electromagnetic energy enters the cuvette is eliminated by the angled reflective surface in the viewing chamber—i.e., reflecting wall 70. By eliminating this backscatter, the volume of the measured sample remains constant, and out-of-focus/blurred image effects that are present in a standard cuvette without the insert are removed.

Second, thermally induced flow resulting from localized thermal gradients generated by the electromagnetic energy can be removed in certain regions of the viewing chamber. Mechanically induced flow from stirring is typically arrested in the viewing chamber within 1 or 2 seconds of stopping the stirring. Without the insert (i.e., in a standard cuvette with no insert), mechanically induced flow from stirring is typically present for 10 seconds after the string is stopped.

Figure 14:
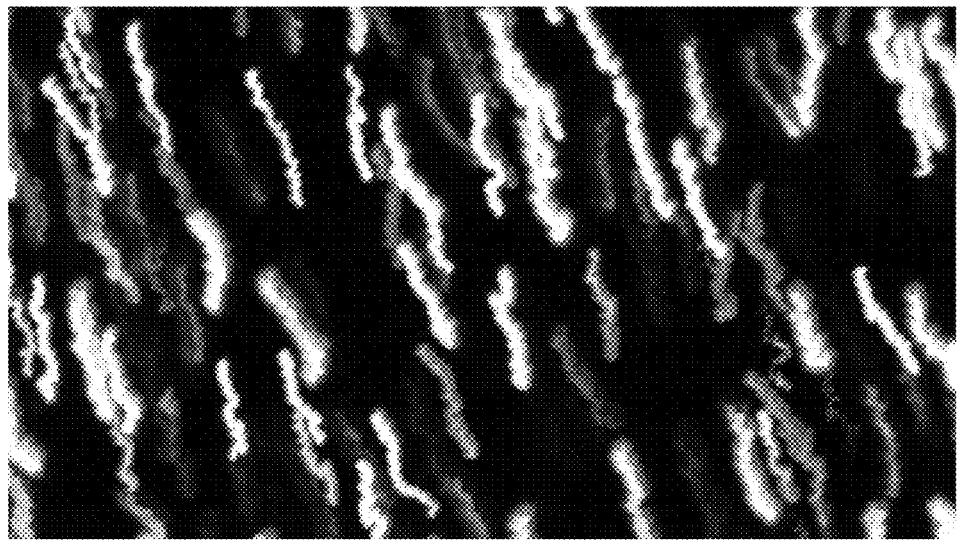
FIG. 14 is a photo showing the movement of particles without the use of the cuvette/insert described herein.
Figure 15:
FIG. 15 is a photo showing the movement of particles with the use of the cuvette/insert described herein.

FIGS. 14 and 15 confirm that the insert does arrest bulk liquid flow. Both FIGS. 14 and 15 are a composite of 300 frames of video showing particles in motion. FIG. 14, where no insert was used, illustrates how particles move primarily with the bulk liquid flow in a substantially linear direction that is common to all the particles. FIG. 15, where the insert is used, illustrates how bulk liquid flow is eliminated such that the only particle movement is through Brownian motion with no discernable pattern common to all the particles. The conditions and the sample are the same in FIGS. 14 and 15—the only change is the inclusion of an insert as disclosed herein.

While the systems, methods and structures described herein have made reference to viewing and analyzing nanoparticles, these same systems, methods and structures may be used for larger particle dimensions, such as micron-sized particles.

Although exemplary embodiments and applications of the invention have been described herein, including as described above and shown in the included example figures, there is no intention that the invention be limited to these exemplary embodiments and applications or to the manner in which the exemplary embodiments and applications operate or are described herein. Indeed, many variations and modifications to the exemplary embodiments are possible, as would be apparent to a person of ordinary skill in the art. The invention may include any device, structure, method, or functionality, as long as the resulting device, system or method falls within the scope of one of the claims that are allowed by the patent office based on this or any related patent application.

The invention claimed is:

1. A system for emitting and detecting electromagnetic radiation of multiple wavelengths to observe the motion of particles in a polydisperse solution in order to size the particles, the system comprising:
   a first light source constructed to emit a first beam of electromagnetic radiation at substantially a first wavelength and directed to a specimen chamber such that a portion of the first beam scatters when illuminating the particles, and wherein the scattered portion of the first beam directed to a sensor;
   a second light source constructed to emit a second beam of electromagnetic radiation at substantially a second wavelength and directed at the specimen chamber such that a portion of the second beam scatters when illuminating the particles, and wherein the scattered portion of the second beam directed to the sensor;
   wherein the first and second wavelengths are different from each other;
   a recorder connected to the sensor;
   a processor connected to the first and second light sources and the recorder, the processor configured to perform the following steps:
      (a) (1) illuminating the specimen chamber with the first beam; (2) preventing the second beam from illuminating the chamber; and (3) simultaneously recording an image including the scattered portion of the first beam from the sensor to an image file;
      (b) after step (a): (1) illuminating the specimen chamber with the second beam; (2) preventing the first beam from illuminating the chamber; and (3) simultaneously recording an image including the scattered portion of the second beam from the sensor to the image file;
      (c) repeating steps (a) and (b) until the expiration of a time period;
      (d) extracting the images from step (a) into a first extracted image file;
      (e) extracting the images from step (b) into a second extracted image file;

(f) determining the size of particles within the first extracted image file by tracking the motion of the particles within the first extracted image file; and
(g) determining the size of particles within the second extracted image file by tracking the motion of the particles within the second extracted image file.

2. The system of claim 1, further comprising a combining structure constructed to merge the first and second beams into the same optical path before either light beam reaches the specimen chamber.

3. The system of claim 1, further comprising a light sheet former that forms the first and second beams into a sheet of electromagnetic radiation directed at the specimen chamber.

4. The system of claim 2, wherein the combining structure is a dichroic mirror.

5. The system of claim 1, further comprising an imaging objective that focuses the scattered portion of the first and second beams onto the sensor.

6. The system of claim 1, wherein the recorder comprises a frame rate, and steps (a)(1) and (b)(1) are performed for an exposure time correlated to the frame rate.

7. The system of claim 1, wherein the sensor is a black-and-white camera.

8. The system of claim 1, wherein the first and second light sources are lasers.

9. The system of claim 1, wherein the wavelengths are selected from a group consisting of red, blue and green.

10. A system for emitting and detecting electromagnetic radiation of multiple wavelengths to observe the motion of particles in a polydisperse solution in order to size the particles, the system comprising:
a first light source constructed to emit a first beam of electromagnetic radiation at substantially a first wavelength and directed to a specimen chamber such that a portion of the first beam scatters when illuminating the particles, and wherein the scattered portion of the first beam directed to a sensor;
a second light source constructed to emit a second beam of electromagnetic radiation at substantially a second wavelength and directed at the specimen chamber such that a portion of the second beam scatters when illuminating the particles, and wherein the scattered portion of the second beam directed to the sensor;
a third light source constructed to emit a third beam of electromagnetic radiation at substantially a third wavelength and directed at the specimen chamber such that a portion of the third beam scatters when illuminating the particles, and wherein the scattered portion of the third beam directed to the sensor;
wherein the first, second and third wavelengths are different from each other;
a recorder connected to the sensor;
a processor connected to the first, second and third light sources and the recorder, the processor configured to perform the following steps:
(a) (1) illuminating the specimen chamber with the first beam; (2) preventing the second and third beams from illuminating the chamber; and (3) simultaneously recording an image including the scattered portion of the first beam from the sensor to an image file;
(b) after step (a): (1) illuminating the specimen chamber with the second beam; (2) preventing the first and third beams from illuminating the chamber; and (3) simultaneously recording an image including the scattered portion of the second beam from the sensor to the image file;
(c) after step (b): (1) illuminating the specimen chamber with the third beam; (2) preventing the second and first beams from illuminating the chamber; and (3) simultaneously recording an image including the scattered portion of the third beam from the sensor to the image file;
(d) repeating steps (a), (b) and (c) until the expiration of a time period;
(e) extracting the images from step (a) into a first extracted image file;
(f) extracting the images from step (b) into a second extracted image file;
(g) extracting the images from step (c) into a third extracted image file; and
(h) determining the size of particles within the first, second and third extracted image files by tracking the motion of the particles within the first, second and third extracted image files, respectively.

11. The system of claim 10, further comprising a combining structure constructed to merge the first, second and third beams into the same optical path before any of the beams reach the specimen chamber.

12. The system of claim 10, further comprising a light sheet former that forms the first, second and third beams into a sheet of electromagnetic radiation directed at the specimen chamber.

13. The system of claim 11, wherein the combining structure is a dichroic mirror.

14. The system of claim 10, further comprising an imaging objective that focuses the scattered portion of the first, second and third beams onto the sensor.

15. The system of claim 10, wherein the recorder comprises a frame rate, and steps (a)(1), (b)(1) and (c)(1) are performed for an exposure time correlated to the frame rate.

16. The system of claim 10, wherein the sensor is a black-and-white camera.

17. The system of claim 10, wherein the first and second light sources are lasers.

18. The system of claim 10, wherein the wavelengths are selected from a group consisting of red, blue and green.

19. A method for time division illumination for use in a system that comprises a first light source constructed to emit a first beam of electromagnetic radiation at substantially a first wavelength, the first beam directed at a specimen chamber that is constructed to allow a portion of the first beam to scatter when illuminating particles within the chamber wherein the scattered portion of the first beam is directed to a sensor, and a second light source constructed to emit a second beam of electromagnetic radiation at substantially a second wavelength, the second beam directed at the specimen chamber such that a portion of the second beam scatters when illuminating the particles wherein the scattered portion of the second beam directed to the sensor, and a recorder connected to the sensor, the method comprising:
(a) (1) illuminating the specimen chamber with the first beam; (2) preventing the second beam from illuminating the chamber; and (3) simultaneously recording an image including the scattered portion of the first beam from the sensor to an image file;
(b) after step (a): (1) illuminating the specimen chamber with the second beam; (2) preventing the first beam from illuminating the chamber; and (3) simultaneously recording an image including the scattered portion of the second beam from the sensor to the image file;
(c) repeating steps (a) and (b) until the expiration of a time period;

(d) extracting the images from step (a) into a first extracted image file;
(e) extracting the images from step (b) into a second extracted image file;
(f) determining the size of particles within the first extracted image file by tracking the motion of the particles within the first extracted image file; and
(g) determining the size of particles within the second extracted image file by tracking the motion of the particles within the second extracted image file.

20. The system of claim 19, wherein the recorder comprises a frame rate, and steps (a)(1) and (b)(1) are performed for an exposure time correlated to the frame rate.

* * * * *